(12) United States Patent
Seligmann et al.

(10) Patent No.: US 9,512,469 B2
(45) Date of Patent: Dec. 6, 2016

(54) METHODS OF CO-DETECTING MRNA AND SMALL NON-CODING RNA

(71) Applicant: HTG Molecular Diagnostics, Inc., Tucson, AZ (US)

(72) Inventors: Bruce Seligmann, Tucson, AZ (US); Matt Rounseville, Tucson, AZ (US); Krishna Maddula, Tucson, AZ (US); Ihab Botros, Tucson, AZ (US); Chris Cox, Tucson, AZ (US)

(73) Assignee: HTG Molecular Diagnostics, Inc., Tucson, AZ (US)

( * ) Notice: Subject to any disclaimer, the term of this patent is extended or adjusted under 35 U.S.C. 154(b) by 0 days.

(21) Appl. No.: 14/347,855

(22) PCT Filed: Sep. 26, 2012

(86) PCT No.: PCT/US2012/057368
§ 371 (c)(1),
(2) Date: Mar. 27, 2014

(87) PCT Pub. No.: WO2013/049231
PCT Pub. Date: Apr. 4, 2013

(65) Prior Publication Data
US 2014/0243238 A1    Aug. 28, 2014

Related U.S. Application Data

(60) Provisional application No. 61/540,387, filed on Sep. 28, 2011.

(51) Int. Cl.
| | | |
|---|---|---|
| C12Q 1/68 | (2006.01) | |
| C12M 1/34 | (2006.01) | |
| C12N 9/22 | (2006.01) | |
| C07H 21/02 | (2006.01) | |
| C07H 21/04 | (2006.01) | |
| G01N 31/22 | (2006.01) | |
| C40B 30/04 | (2006.01) | |

(52) U.S. Cl.
CPC .................................. C12Q 1/6816 (2013.01)

(58) Field of Classification Search
CPC ........................................................ C12Q 1/68
USPC ........... 435/6.1, 91.53, 199, 287.2; 536/23.1, 536/24.3; 422/430; 506/9
See application file for complete search history.

(56) References Cited

U.S. PATENT DOCUMENTS

| | | | |
|---|---|---|---|
| 6,228,580 B1 * | 5/2001 | Blumenfeld et al. ........ | 435/6.12 |
| 7,413,852 B2 | 8/2008 | Balch | |
| 2003/0096232 A1 | 5/2003 | Kris et al. | |
| 2003/0170623 A1 * | 9/2003 | Chen et al. ................... | 435/6 |
| 2006/0078925 A1 | 4/2006 | Mourelatos et al. | |

FOREIGN PATENT DOCUMENTS

| | | |
|---|---|---|
| WO | WO 98/29736 | 7/1998 |
| WO | WO 03/002750 | 1/2003 |
| WO | WO 2006/042303 | 4/2006 |
| WO | WO 2008/121927 | 10/2008 |
| WO | WO 2010/115833 | 10/2010 |
| WO | WO 2011/056863 | 5/2011 |

OTHER PUBLICATIONS

Young, Cytokine Multiplex Analysis, Inflammation and Cancer, Methods in Molecular Biology, 2009, 511, 85-105.*
Cho, "Great potential of miRNAs as predictive and prognostic markers for cancer," *Expert Rev. Mol. Diagn.*, vol. 12, No. 4, pp. 315-318, 2012.
de Jonge et al., "Evidence Based Selection of Housekeeping Genes," *PLoS ONE*, 9(2):e898, 2007 (5 pages).
Eisenberg et al., "Human housekeeping genes are compact," *TRENDS in Genetics*, vol. 19, No. 7, pp. 362-365, 2003.
Geiss et al., "Direct multiplexed measurement of gene expression with color-coded probe pairs," *Nature Biotechnology*, vol. 26, pp. 317-325, 2008 (Abstract only, 3 pages).
Iorio et al, "MicroRNA dysregulation in cancer: diagnostics, monitoring and therapeutics. A comprehensive review," *EMBO Molecular Medicine*, vol. 4, pp. 143-159, 2012.
Kouadjo et al., "Housekeeping and tissue-specific genes in mouse tissues," *BMC Genomics*, 8:127, 2007 (16 pages).
McGregor et al., "microRNAs in the Regulation of Adipogenesis and Obesity," *Current Molecular Medicine*, vol. 11, pp. 304-316, 2011.
miRNA on the qNPA™ ArrayPlate, High Throughput Genomics, Inc., 2011 (5 pages).
mirVana™ miRNA Detection Kit, Ambion, Inc., 2011 (39 pages).
nanoString® Product Data Sheet, nCounter® miRGE Assay CodeSet, 2012 (4 pages).
Romao et al., "MicroRNA regulation in mammalian adipogenesis," *Experimental Biology and Medicine*, vol. 236, pp. 997-1004, 2011.

(Continued)

*Primary Examiner* — Narayan Bhat
(74) *Attorney, Agent, or Firm* — Klarquist Sparkman, LLP

(57) ABSTRACT

Disclosed herein are methods of co-detecting presence of target messenger RNA (mRNA) and small non-coding RNA (for example, miRNA) in a sample. The disclosed methods can be used to simultaneously detect mRNA and small non-coding RNA in a single assay (for example in the same reaction or the same well of a multi-well assay). The methods can include contacting a sample with a plurality of nuclease protection probes (NPPs) including at least one probe which specifically binds to a target mRNA and at least one probe which specifically binds to a target small non-coding RNA, contacting the sample with a nuclease specific for single-stranded nucleic acids, and detecting the NPP, for example on a microarray.

22 Claims, 4 Drawing Sheets

(56) References Cited

OTHER PUBLICATIONS

Sana et al., "Novel classes of non-coding RNAs and cancer," *Journal of Translational Medicine*, 10:103, 2012 (21 pages).
Saviozzi et al., "Selection of suitable reference genes for accurate normalization of gene expression profile studies in non-small cell lung cancer," BMC Cancer, 6:200, 2006 (10 pages).
Subramanyam et al., "From microRNAs to targets: pathway discovery in cell fate transitions," *Curr. Opin, Genet. Dev.*, vol. 21, No. 4, pp. 498-503, 2011 (12 pages, author manuscript version).
Zhang et al., "Mammalian Housekeeping Genes Evolve More Slowly than Tissue-Specific Genes," *Mol. Biol. Evol.*, vol. 21, No. 2, pp. 236-239, 2004.
Martel et al., "Multiplexed Screening Assay for mRNA Combining Nuclease Protection with Luminescent Array Detection," *ASSAY and Drug Development Technologies*, vol. 1, No. 1-1, pp. 61-71, 2002.

\* cited by examiner

SEQUENCE LISTING

<160> NUMBER OF SEQ ID NOS: 56

<210> SEQ ID NO 1
<211> LENGTH: 16
<212> TYPE: DNA
<213> ORGANISM: Artificial Sequence
<220> FEATURE:
<223> OTHER INFORMATION: Synthetic oligonucleotide anchor

<400> SEQUENCE: 1
tgattcagac cggccg                                               16

<210> SEQ ID NO 2
<211> LENGTH: 16
<212> TYPE: DNA
<213> ORGANISM: Artificial Sequence
<220> FEATURE:
<223> OTHER INFORMATION: Synthetic oligonucleotide anchor

<400> SEQUENCE: 2
cccggggcgt cttaac                                               16

<210> SEQ ID NO 3
<211> LENGTH: 16
<212> TYPE: DNA
<213> ORGANISM: Artificial Sequence
<220> FEATURE:
<223> OTHER INFORMATION: Synthetic oligonucleotide anchor

<400> SEQUENCE: 3
ggacgccata tgcgct                                               16

<210> SEQ ID NO 4
<211> LENGTH: 16
<212> TYPE: DNA
<213> ORGANISM: Artificial Sequence
<220> FEATURE:
<223> OTHER INFORMATION: Synthetic oligonucleotide anchor

<400> SEQUENCE: 4
tgagggctcc gccata                                               16

<210> SEQ ID NO 5
<211> LENGTH: 16
<212> TYPE: DNA
<213> ORGANISM: Artificial Sequence
<220> FEATURE:
<223> OTHER INFORMATION: Synthetic oligonucleotide anchor

<400> SEQUENCE: 5
aacccgtgac gtgtgc                                               16

<210> SEQ ID NO 6
<211> LENGTH: 16
<212> TYPE: DNA
<213> ORGANISM: Artificial Sequence
<220> FEATURE:
<223> OTHER INFORMATION: Synthetic oligonucleotide anchor

<400> SEQUENCE: 6
agcatcgccg gtcctg                                               16

<210> SEQ ID NO 7
<211> LENGTH: 16
<212> TYPE: DNA
<213> ORGANISM: Artificial Sequence

```
<220> FEATURE:
<223> OTHER INFORMATION: Synthetic oligonucleotide anchor

<400> SEQUENCE: 7
cctgcaaggc tgacgt                                                 16

<210> SEQ ID NO 8
<211> LENGTH: 16
<212> TYPE: DNA
<213> ORGANISM: Artificial Sequence
<220> FEATURE:
<223> OTHER INFORMATION: Synthetic oligonucleotide anchor.

<400> SEQUENCE: 8
cagttgtcga ccccgg                                                 16

<210> SEQ ID NO 9
<211> LENGTH: 16
<212> TYPE: DNA
<213> ORGANISM: Artificial Sequence
<220> FEATURE:
<223> OTHER INFORMATION: Synthetic oligonucleotide anchor

<400> SEQUENCE: 9
cggcgcgtcc aattcg                                                 16

<210> SEQ ID NO 10
<211> LENGTH: 16
<212> TYPE: DNA
<213> ORGANISM: Artificial Sequence
<220> FEATURE:
<223> OTHER INFORMATION: Synthetic oligonucleotide anchor

<400> SEQUENCE: 10
atcgatctga gggccc                                                 16

<210> SEQ ID NO 11
<211> LENGTH: 16
<212> TYPE: DNA
<213> ORGANISM: Artificial Sequence
<220> FEATURE:
<223> OTHER INFORMATION: Synthetic oligonucleotide anchor

<400> SEQUENCE: 11
gtacatgcgg cctgca                                                 16

<210> SEQ ID NO 12
<211> LENGTH: 16
<212> TYPE: DNA
<213> ORGANISM: Artificial Sequence
<220> FEATURE:
<223> OTHER INFORMATION: Synthetic oligonucleotide anchor

<400> SEQUENCE: 12
tagccgctcg ctagag                                                 16

<210> SEQ ID NO 13
<211> LENGTH: 16
<212> TYPE: DNA
<213> ORGANISM: Artificial Sequence
<220> FEATURE:
<223> OTHER INFORMATION: Synthetic oligonucleotide anchor

<400> SEQUENCE: 13
cctagtgatg accggc                                                 16
```

<210> SEQ ID NO 14
<211> LENGTH: 16
<212> TYPE: DNA
<213> ORGANISM: Artificial Sequence
<220> FEATURE:
<223> OTHER INFORMATION: Synthetic oligonucleotide anchor

<400> SEQUENCE: 14
gtctgagggc aacctc                                                    16

<210> SEQ ID NO 15
<211> LENGTH: 16
<212> TYPE: DNA
<213> ORGANISM: Artificial Sequence
<220> FEATURE:
<223> OTHER INFORMATION: Synthetic oligonucleotide anchor

<400> SEQUENCE: 15
ctagctggct acgcag                                                    16

<210> SEQ ID NO 16
<211> LENGTH: 16
<212> TYPE: DNA
<213> ORGANISM: Artificial Sequence
<220> FEATURE:
<223> OTHER INFORMATION: Synthetic oligonucleotide anchor

<400> SEQUENCE: 16
gccatccgct tggagc                                                    16

<210> SEQ ID NO 17
<211> LENGTH: 25
<212> TYPE: DNA
<213> ORGANISM: Artificial Sequence
<220> FEATURE:
<223> OTHER INFORMATION: Synthetic oligonucleotide GAPDH probe

<400> SEQUENCE: 17
ccgttgactc cgaccttcac cttcc                                          25

<210> SEQ ID NO 18
<211> LENGTH: 25
<212> TYPE: DNA
<213> ORGANISM: Artificial Sequence
<220> FEATURE:
<223> OTHER INFORMATION: Synthetic oligonucleotide PPIA probe

<400> SEQUENCE: 18
acacaagact gagatgcaca agtgg                                          25

<210> SEQ ID NO 19
<211> LENGTH: 25
<212> TYPE: DNA
<213> ORGANISM: Artificial Sequence
<220> FEATURE:
<223> OTHER INFORMATION: Synthetic oligonucleotide RPLP0 probe

<400> SEQUENCE: 19
gacagacact ggcaacattg cggac                                          25

<210> SEQ ID NO 20
<211> LENGTH: 25
<212> TYPE: DNA
<213> ORGANISM: Artificial Sequence
<220> FEATURE:
<223> OTHER INFORMATION: Synthetic oligonucleotide RPL19 probe

```
<400> SEQUENCE: 20
aagcctgagc atactcatgg ctgcg                                          25

<210> SEQ ID NO 21
<211> LENGTH: 25
<212> TYPE: DNA
<213> ORGANISM: Artificial Sequence
<220> FEATURE:
<223> OTHER INFORMATION: Synthetic oligonucleotide ZEB1 probe

<400> SEQUENCE: 21
aaaggcatct aaacccaggc ttccc                                          25

<210> SEQ ID NO 22
<211> LENGTH: 25
<212> TYPE: DNA
<213> ORGANISM: Artificial Sequence
<220> FEATURE:
<223> OTHER INFORMATION: Synthetic oligonucleotide ZEB2 probe

<400> SEQUENCE: 22
cttgtgtgtc accatatgcc gctcg                                          25

<210> SEQ ID NO 23
<211> LENGTH: 25
<212> TYPE: DNA
<213> ORGANISM: Artificial Sequence
<220> FEATURE:
<223> OTHER INFORMATION: Synthetic oligonucleotide CDH1 probe

<400> SEQUENCE: 23
ccaaagtcct cggacacttc cactc                                          25

<210> SEQ ID NO 24
<211> LENGTH: 25
<212> TYPE: DNA
<213> ORGANISM: Artificial Sequence
<220> FEATURE:
<223> OTHER INFORMATION: Synthetic oligonucleotide CDH2 probe

<400> SEQUENCE: 24
tccgccactg attctgtaca ctgcg                                          25

<210> SEQ ID NO 25
<211> LENGTH: 25
<212> TYPE: DNA
<213> ORGANISM: Artificial Sequence
<220> FEATURE:
<223> OTHER INFORMATION: Synthetic oligonucleotide ACTA2 probe

<400> SEQUENCE: 25
acacatagct ggagctgctt cacag                                          25

<210> SEQ ID NO 26
<211> LENGTH: 25
<212> TYPE: DNA
<213> ORGANISM: Artificial Sequence
<220> FEATURE:
<223> OTHER INFORMATION: Synthetic oligonucleotide CTNNB1 probe

<400> SEQUENCE: 26
tgtgaagggc tccggtacaa ccttc                                          25

<210> SEQ ID NO 27
```

```
<211> LENGTH: 25
<212> TYPE: DNA
<213> ORGANISM: Artificial Sequence
<220> FEATURE:
<223> OTHER INFORMATION: Synthetic oligonucleotide KRT8 probe

<400> SEQUENCE: 27
cagcttccca tcacgtgtct cgatc                                          25

<210> SEQ ID NO 28
<211> LENGTH: 25
<212> TYPE: DNA
<213> ORGANISM: Artificial Sequence
<220> FEATURE:
<223> OTHER INFORMATION: Synthetic oligonucleotide SNAI1 probe

<400> SEQUENCE: 28
gacattcggg agaaggtccg agcac                                          25

<210> SEQ ID NO 29
<211> LENGTH: 25
<212> TYPE: DNA
<213> ORGANISM: Artificial Sequence
<220> FEATURE:
<223> OTHER INFORMATION: Synthetic oligonucleotide SNAI2 probe

<400> SEQUENCE: 29
ttgggtagct gggcgtggaa tggag                                          25

<210> SEQ ID NO 30
<211> LENGTH: 25
<212> TYPE: DNA
<213> ORGANISM: Artificial Sequence
<220> FEATURE:
<223> OTHER INFORMATION: Synthetic oligonucleotide TWIST1 probe

<400> SEQUENCE: 30
cccgtctggg aatcactgtc cacgg                                          25

<210> SEQ ID NO 31
<211> LENGTH: 25
<212> TYPE: DNA
<213> ORGANISM: Artificial Sequence
<220> FEATURE:
<223> OTHER INFORMATION: Synthetic oligonucleotide FN1 probe

<400> SEQUENCE: 31
gctgaacatt gggtggtgtc cactg                                          25

<210> SEQ ID NO 32
<211> LENGTH: 25
<212> TYPE: DNA
<213> ORGANISM: Artificial Sequence
<220> FEATURE:
<223> OTHER INFORMATION: Synthetic oligonucleotide EPAS1 probe

<400> SEQUENCE: 32
cccttggtgc acaagttctg gtgac                                          25

<210> SEQ ID NO 33
<211> LENGTH: 25
<212> TYPE: DNA
<213> ORGANISM: Artificial Sequence
<220> FEATURE:
<223> OTHER INFORMATION: Synthetic oligonucleotide ESR2 probe

<400> SEQUENCE: 33
```

-continued

```
acaaagccgg gaatcttctt ggccc                                              25

<210> SEQ ID NO 34
<211> LENGTH: 25
<212> TYPE: DNA
<213> ORGANISM: Artificial Sequence
<220> FEATURE:
<223> OTHER INFORMATION: Synthetic oligonucleotide PRKCE probe

<400> SEQUENCE: 34
cctcagatgg tgagcttcca gaagc                                              25

<210> SEQ ID NO 35
<211> LENGTH: 25
<212> TYPE: DNA
<213> ORGANISM: Artificial Sequence
<220> FEATURE:
<223> OTHER INFORMATION: Synthetic oligonucleotide EZH2 probe

<400> SEQUENCE: 35
tcagatttct tcccagtctg gccca                                              25

<210> SEQ ID NO 36
<211> LENGTH: 25
<212> TYPE: DNA
<213> ORGANISM: Artificial Sequence
<220> FEATURE:
<223> OTHER INFORMATION: Synthetic oligonucleotide DAB2IP probe

<400> SEQUENCE: 36
cctcgaagca gtagtcctgg ccaag                                              25

<210> SEQ ID NO 37
<211> LENGTH: 25
<212> TYPE: DNA
<213> ORGANISM: Artificial Sequence
<220> FEATURE:
<223> OTHER INFORMATION: Synthetic oligonucleotide B2M probe

<400> SEQUENCE: 37
ctaaggccac ggagcgagac atctc                                              25

<210> SEQ ID NO 38
<211> LENGTH: 25
<212> TYPE: DNA
<213> ORGANISM: Artificial Sequence
<220> FEATURE:
<223> OTHER INFORMATION: Synthetic oligonucleotide SDHA probe

<400> SEQUENCE: 38
ccagtgctcc tcaaagggct tcttc                                              25

<210> SEQ ID NO 39
<211> LENGTH: 22
<212> TYPE: DNA
<213> ORGANISM: Artificial Sequence
<220> FEATURE:
<223> OTHER INFORMATION: Synthetic oligonucleotide hsa-miR-205 probe

<400> SEQUENCE: 39
cagactccgg tggaatgaag ga                                                 22

<210> SEQ ID NO 40
<211> LENGTH: 23
<212> TYPE: DNA
```

```
<213> ORGANISM: Artificial Sequence
<220> FEATURE:
<223> OTHER INFORMATION: Synthetic oligonucleotide hsa-miR-324-5p probe

<400> SEQUENCE: 40
acaccaatgc cctaggggat gcg                                              23

<210> SEQ ID NO 41
<211> LENGTH: 23
<212> TYPE: DNA
<213> ORGANISM: Artificial Sequence
<220> FEATURE:
<223> OTHER INFORMATION: Synthetic oligonucleotide hsa-miR-301a

<400> SEQUENCE: 41
gctttgacaa tactattgca ctg                                              23

<210> SEQ ID NO 42
<211> LENGTH: 21
<212> TYPE: DNA
<213> ORGANISM: Artificial Sequence
<220> FEATURE:
<223> OTHER INFORMATION: Synthetic oligonucleotide hsa-miR-106b

<400> SEQUENCE: 42
atctgcactg tcagcacttt a                                                21

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide hsa-miR-877 probe

<400> SEQUENCE: 43
ccctgcgcca tctcctctac                                                  20

<210> SEQ ID NO 44
<211> LENGTH: 23
<212> TYPE: DNA
<213> ORGANISM: Artificial Sequence
<220> FEATURE:
<223> OTHER INFORMATION: Synthetic oligonucleotide hsa-miR-339-3p probe

<400> SEQUENCE: 44
cggctctgtc gtcgaggcgc tca                                              23

<210> SEQ ID NO 45
<211> LENGTH: 23
<212> TYPE: DNA
<213> ORGANISM: Artificial Sequence
<220> FEATURE:
<223> OTHER INFORMATION: Synthetic oligonucleotide hsa-miR-10b probe

<400> SEQUENCE: 45
cacaaattcg gttctacagg gta                                              23

<210> SEQ ID NO 46
<211> LENGTH: 22
<212> TYPE: DNA
<213> ORGANISM: Artificial Sequence
<220> FEATURE:
<223> OTHER INFORMATION: Synthetic oligonucleotide hsa-miR-185 probe

<400> SEQUENCE: 46
tcaggaactg cctttctctc ca                                               22
```

<210> SEQ ID NO 47
<211> LENGTH: 22
<212> TYPE: DNA
<213> ORGANISM: Artificial Sequence
<220> FEATURE:
<223> OTHER INFORMATION: Synthetic oligonucleotide hsa-miR-27b probe

<400> SEQUENCE: 47
gttcaccaat cagctaagct ct                                            22

<210> SEQ ID NO 48
<211> LENGTH: 23
<212> TYPE: DNA
<213> ORGANISM: Artificial Sequence
<220> FEATURE:
<223> OTHER INFORMATION: Synthetic oligonucleotide hsa-miR-492 probe

<400> SEQUENCE: 48
aagaatcttg tcccgcaggt cct                                           23

<210> SEQ ID NO 49
<211> LENGTH: 22
<212> TYPE: DNA
<213> ORGANISM: Artificial Sequence
<220> FEATURE:
<223> OTHER INFORMATION: Synthetic oligonucleotide hsa-miR-146a probe

<400> SEQUENCE: 49
aacccatgga attcagttct ca                                            22

<210> SEQ ID NO 50
<211> LENGTH: 22
<212> TYPE: DNA
<213> ORGANISM: Artificial Sequence
<220> FEATURE:
<223> OTHER INFORMATION: Synthetic oligonucleotide hsa-miR-200a probe

<400> SEQUENCE: 50
tccagcactg tccggtaaga tg                                            22

<210> SEQ ID NO 51
<211> LENGTH: 25
<212> TYPE: DNA
<213> ORGANISM: Artificial Sequence
<220> FEATURE:
<223> OTHER INFORMATION: Synthetic oligonucleotide ANT probe

<400> SEQUENCE: 51
gttgtgatgg gtcccaaaga aatcc                                         25

<210> SEQ ID NO 52
<211> LENGTH: 23
<212> TYPE: DNA
<213> ORGANISM: Artificial Sequence
<220> FEATURE:
<223> OTHER INFORMATION: Synthetic oligonucleotide hsa-miR-339-5p probe

<400> SEQUENCE: 52
cgtgagctcc tggaggacag gga                                           23

<210> SEQ ID NO 53
<211> LENGTH: 23
<212> TYPE: DNA
<213> ORGANISM: Artificial Sequence
<220> FEATURE:

```
<223> OTHER INFORMATION: Synthetic oligonucleotide hsa-miR-30c

<400> SEQUENCE: 53
gctgagagtg taggatgttt aca                                          23

<210> SEQ ID NO 54
<211> LENGTH: 22
<212> TYPE: DNA
<213> ORGANISM: Artificial Sequence
<220> FEATURE:
<223> OTHER INFORMATION: Synthetic oligonucleotide hsa-miR-29c probe

<400> SEQUENCE: 54
gaacaccagg agaaatcggt ca                                           22

<210> SEQ ID NO 55
<211> LENGTH: 23
<212> TYPE: DNA
<213> ORGANISM: Artificial Sequence
<220> FEATURE:
<223> OTHER INFORMATION: Synthetic oligonucleotide hsa-miR-191 probe

<400> SEQUENCE: 55
cagctgcttt tgggattccg ttg                                          23

<210> SEQ ID NO 56
<211> LENGTH: 22
<212> TYPE: DNA
<213> ORGANISM: Artificial Sequence
<220> FEATURE:
<223> OTHER INFORMATION: Synthetic oligonucleotide hsa-miR-655 probe

<400> SEQUENCE: 56
aaagaggtta accatgtatt at                                           22
```

METHODS OF CO-DETECTING MRNA AND SMALL NON-CODING RNA

CROSS REFERENCE TO RELATED APPLICATION

This is the §371 U.S. National Stage of International Application No. PCT/US2012/057368, filed Sep. 26,2012, which was published in English under PCT Article 21(2), which in turn claims the benefit of U.S. Provisional Application No. 61/540,387, filed Sep. 28, 2011, which is incorporated herein by reference in its entirety.

ACKNOWLEDGMENT OF GOVERNMENT SUPPORT

This invention was made with government support under 1R43A1078577-01A1 awarded by National Institutes of Health. The government has certain rights in the invention.

FIELD

This disclosure relates to methods of detecting nucleic acids, particularly detecting messenger RNA and small non-coding RNA in a sample.

BACKGROUND

While almost all cells in an organism contain the entire genome of the organism, only a relatively small subset of the genes in the genome is expressed at any given time in a given cell population, and different cell populations exhibit very different patterns of gene expression. These different expression patterns are responsible for the varied characteristics of cells and tissues, both in health and disease.

Transcription of the genome in a cell or sample type of interest produces an abundant population of RNA transcripts called the transcriptome. The transcriptome includes messenger RNAs, which, generally, are translated into protein, as well as a variety of non-coding RNAs. Gene expression profiling, which contemporaneously examines a plurality of expressed mRNAs in a sample, arose from the desire to understand and characterize the transcriptome. By collecting and comparing gene expression profiles of different types of cells, medical science has gained a deeper understanding of what constitutes a specific cell type, how that type of cell normally functions, and how changes in the normal level of gene activity may reflect or contribute to disease.

Until relatively recently, non-coding RNAs in the transcriptome (such as small, non-coding RNAs, e.g., miRNA, siRNA, or piRNA) received much less attention than did protein-coding mRNAs. Recent progress suggests that the involvement of non-coding RNAs in human diseases could be far more prevalent than previously appreciated (e.g., Cho, *Expert Rev. Mol. Diagn.* 12:315-318, 2012; Sana et al., *J. Translational Med.* 10:103, 2012). Multiple lines of evidence increasingly link mutations and dysregulations of non-coding RNAs to diverse human diseases, ranging from neurodegeneration to cancer (e.g., Iorio and Croce, *EMBO Mol. Med.* 4:143-159, 2012).

As one example, miRNAs are short approximately 22 nucleotide RNA sequences that bind to complementary sequences in multiple target mRNAs, usually resulting in mRNA silencing. miRNAs have many functions in physiology, from cell differentiation, proliferation, apoptosis to the endocrine system, hematopoiesis, fat metabolism, and limb morphogenesis (e.g., Romao et al., *Exp. Biol. Med.* 236:997-1004, 2011; Subramanyam and Blelloch, *Curr. Opin. Genet. Dev.* 21:498-503, 2011; McGregor and Choi, *Curr. Mol. Med.* 11:304-316, 2011; Fernandez-Hernando et al., *Curr. Opin. Lipidol.* 22:86-92, 2011). Like mRNAs, miRNAs display different expression profiles from tissue to tissue.

It is clear that a more comprehensive view of the transcriptome, including the expression of both mRNA and non-coding RNAs (such as small, non-coding RNAs, e.g., miRNA, siRNA, or piRNA) is needed. Unfortunately, these members of the transcriptome often have different properties (e.g., size) that make it difficult to detect them contemporaneously in the same sample. To avoid sample-to-sample artifacts caused by measuring mRNA in one sample and miRNA (or other small non-coding RNAs) in another, new methods are needed to spur and support growth of global transcriptome analysis.

SUMMARY

Disclosed herein are methods of co-detecting presence of target messenger RNA (mRNA) and target small non-coding RNA (such as microRNA (miRNA)) in a sample. Particularly advantageous embodiments of the disclosed methods permit multiplex detection of mRNA and miRNA utilizing a quantitative nuclease protection (qNPA) assay. The disclosed methods can be used to detect mRNA and small non-coding RNA (such as miRNA) in a single assay (for example in the same reaction and/or the same well of a multi-well assay). The methods are highly sensitive and specific and optionally can be used to quantify detected mRNA and small non-coding RNA. The disclosed methods are also amenable to multiplexing, so as to detect multiple mRNAs and small non-coding RNAs (such as miRNAs) in samples from one or more subjects.

The foregoing and other features of the disclosure will become more apparent from the following detailed description, which proceeds with reference to the accompanying figures.

SEQUENCE LISTING

Figure 1:
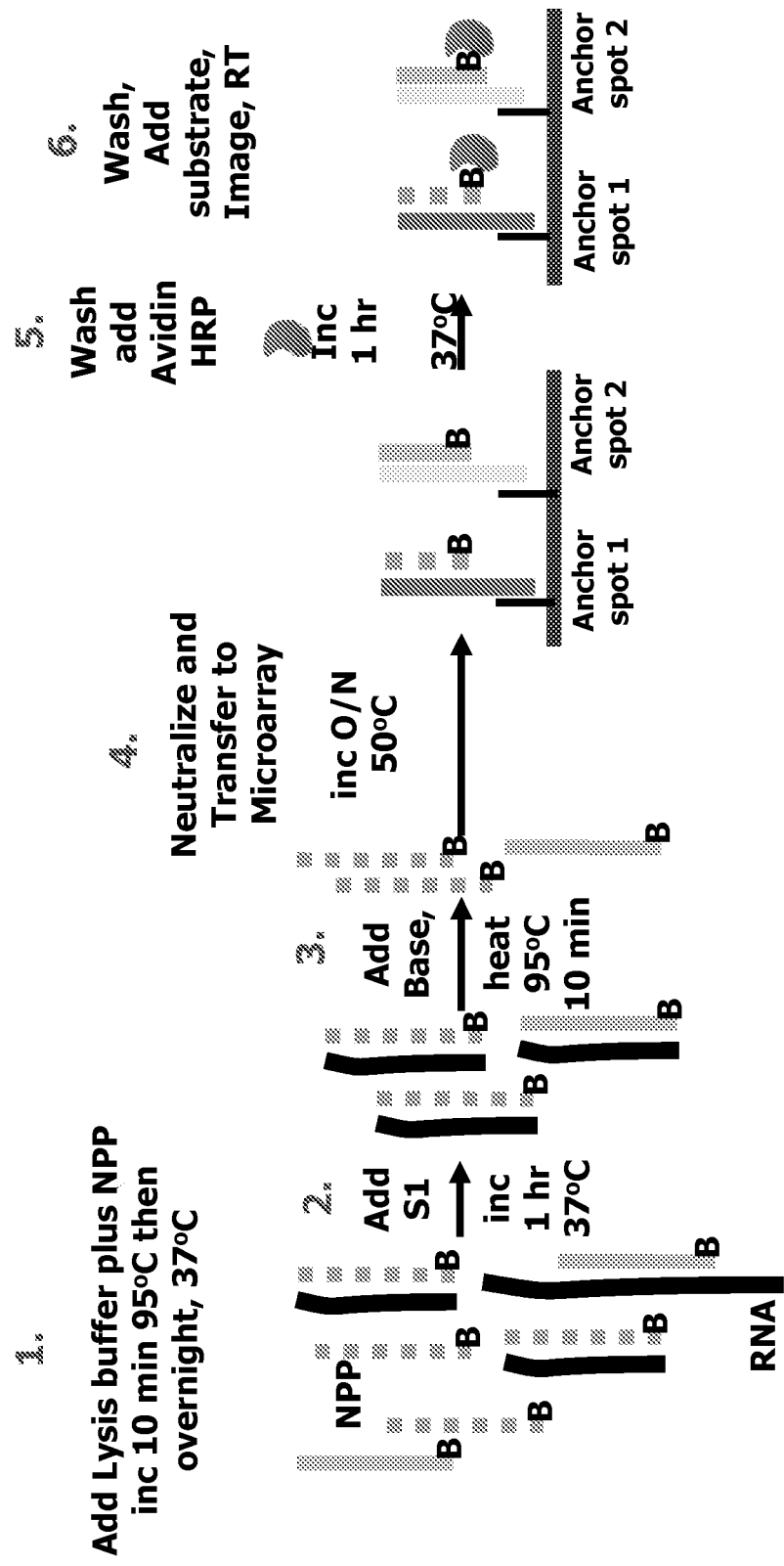
FIG. 1 is a schematic diagram showing an exemplary quantitative nuclease protection assay protocol used to measure mRNA and miRNA at the same time, on the same array. The dashed bars represent a nuclease protection probe (NPP) for miRNA labeled with biotin (B), the solid gray bars represent NPP for mRNA labeled with biotin (B), and the solid black bars represent RNA (either mRNA or miRNA). (1) A sample (such as cells or FFPE tissue) is lysed and incubated with the NPPs. (2) Unbound (e.g., single-stranded) nucleic acid is digested with S1 nuclease, and then the NPPs are dissociated by (3) addition of base and heating. (4) The NPPs are captured on an array including bifunctional (programming) linkers associated with anchors. (5) Avidin-horseradish peroxidase (HRP) is used to detect the bound NPPs and (6) the entire microplate is imaged following addition of substrate. The location of the signal on the array allows identification of signal generated by a target mRNA or target miRNA.

Any nucleic acid and amino acid sequences listed herein or in the accompanying sequence listing are shown using standard letter abbreviations for nucleotide bases, and three letter code for amino acids, as defined in 37 C.F.R. §1.822. In at least some cases, only one strand of each nucleic acid sequence is shown, but the complementary strand is understood as included by any reference to the displayed strand. In the provided sequences:

SEQ ID NOs: 1-16 are exemplary anchor nucleic acid sequences.

SEQ ID NOs: 17-56 are exemplary mRNA and miRNA NPP nucleic acid sequences.

The Sequence Listing is submitted as an ASCII text file in the form of the file named Sequence$_{13}$ Listing.txt, which was created on Mar. 25, 2014, and is 12,181 bytes, which is incorporated by reference herein.

DETAILED DESCRIPTION

Disclosed herein are methods of co-detecting (e.g., simultaneously or substantially simultaneously, contemporaneously, or concurrently) detecting mRNA and small non-coding RNA (such as miRNA, siRNA, piRNA, tiRNA, crasiRNA, or tel-sRNA) in a sample, for example detecting mRNA and small non-coding RNA in the same sample or same assay (for example, in the reaction and/or the same well of an assay plate). In some embodiments, the methods include contacting a sample with a plurality of NPPs including at least one NPP which specifically binds to a target mRNA and at least one NPP which specifically binds to a target small non-coding RNA (such as an miRNA) under conditions sufficient for each of the NPPs to bind to its target mRNA or small non-coding RNA, wherein each of the plurality of NPPs includes a detectable label. The sample is contacted with a nuclease specific for single-stranded nucleic acid molecules under conditions sufficient to remove (for example, digest) unbound nucleic acid molecules. The mRNA or small non-coding RNA is identified as present in the sample when its respective NPP is detected.

In some embodiments, the disclosed methods permit co-detection or simultaneous detection of mRNA and miRNA, which has been difficult or even impossible using prior methods. In standard methods of detecting mRNA and miRNA, mRNA probes are longer than the longest miRNA probe (which is limited by the length of the miRNA), thus binding kinetics of the two probe types differ and make co-detection or simultaneous detection difficult, particularly for accurate and reproducible target-to-target quantitation within the same sample or cross-sample comparisons. In some embodiments, the disclosed methods utilize mRNA and miRNA probes of the same or similar length (for example NPPs of about 15 to 30 nucleotides, such as about 20 to 25 nucleotides), permitting accurate and reproducible co-detection of both mRNA and miRNA (for example, in the same reaction). In some examples, the methods include contacting a sample with a plurality of NPPs including at least one NPP which specifically binds to a target mRNA and at least one NPP which specifically binds to a target miRNA under conditions sufficient for each of the NPPs to bind to its target mRNA or miRNA, wherein each of the plurality of NPPs includes a detectable label. The sample is contacted with a nuclease specific for single-stranded nucleic acid molecules under conditions sufficient to remove (for example, digest) unbound nucleic acid molecules. The mRNA or miRNA is identified as present in the sample when its respective NPP is detected.

In some embodiments, the nuclease-treated sample is contacted with a surface (e.g., a substrate) including multiple spatially discrete regions, each of which include at least one anchor in association with a bifunctional linker including a first portion which specifically binds to the anchor and a second portion which specifically binds to one of the plurality of NPPs, under conditions sufficient for each of the plurality of NPPs to specifically bind to the second portion of a bifunctional linker. The NPP bound to the second portion of the bifunctional linker is detected utilizing the detectable label included in the NPP, thereby detecting target mRNA and small non-coding RNA (such as miRNA) in the sample.

In other embodiments, the NPPs can be detected utilizing a multiwell plate or other array, such as a microarray (e.g., a NIMBLEGEN microarray; Roche Nimblegen, Madison, Wis.) or the NPPs can be captured on beads or other particles (e.g., X-MAP beads from Luminex, Austin, Tex.) or a QBEAD assay.

The inclusion of a nuclease protection step in the disclosed methods can reduce the need for extensive handling of nucleic acids, particularly RNA, which can be sensitive to degradation by contaminating nucleases and thus difficult to work with. In particular embodiments, the disclosed methods do not require sample preparation beyond cell lysis. For example, extraction of nucleic acids is not required. A particular advantage of "lysis only" methods disclosed herein is that all or substantially all of the RNA population (including both mRNA and small non-coding RNA) is included in the assay. The use of a "lysis only" protocol assures that there is little or no bias toward retention of one species over another in the sample (for example mRNA versus miRNA). This decreases the loss of particular RNAs or populations of RNAs (for example short RNAs, such as miRNAs or other small non-coding RNAs) during sample preparation. Extraction protocols inherently include the possibility that the efficiency of recovery of longer nucleic acids (such as mRNAs) is different than that of shorter nucleic acids (such as miRNAs). In addition, by eliminating the need for nucleic acid purification (before or after probe hybridization), interassay variability introduced by nucleic acid extraction steps is decreased. Finally, lysis-only embodiments permit the ability to measure both soluble nucleic acids as well as cross-linked nucleic acids (for example in formalin-fixed paraffin-embedded (FFPE) sections). Elimination of interassay variability is particularly advantageous in the case of FFPE samples, due to variations in cellularity, necrosis, and/or percent of target (e.g., tumor cells) from patient to patient and even between sections from a single patient. Thus, a method that permits measurement of mRNA and miRNA from the same FFPE sample can further reduce variability and increase sensitivity and specificity of assays.

In addition, the nuclease protection step provides a quantitative assay, wherein the NPPs remaining following nuclease digestion are a stoichiometric reflection of the complementary nucleic acid species in the original sample. This eliminates the possibility of differences in probe processing and permits multiplexing to a very high degree. In particular, the disclosed methods permit multiplexing to detect both mRNA and small non-coding RNA species, and can further include detection of additional nucleic acid species, including genomic DNA, cDNA, tRNA, snRNA, snoRNA, and/or rRNA.

Nuclease protection of a sample can allow for greater sensitivity and reproducibility in an assay. In some embodiments, the methods result in decreased background and complexity (e.g., which can lead to cross-hybridization), for example, because nuclease treatment destroys most non-specifically hybridized nucleic acids. Thus, the disclosed assays can be sensitive enough such that amplification of target mRNAs and miRNAs is not necessary in order to detect a signal. In a particular example, sensitivity of detection of mRNA and miRNA in FFPE samples is very high utilizing the disclosed methods because cross-linked target RNA does not need to be extracted (a highly inefficient and destructive process), but rather NPP hybridize directly to the cross-linked RNA. Following nuclease digestion, the NPPs can be dissociated and solubilized for quantification by simple denaturation.

Particular method embodiments specifically do not include an amplification (e.g., PCR amplification) step. This reduces drawbacks of an amplification step, such as sequence-specific artifacts or bias, limited dynamic range, and the necessity for using purified and intact nucleic acids. The increased sensitivity of the disclosed methods allow for multiple assays to be performed on a single sample (for example, a single sample or FFPE section can be divided into multiple tests). Furthermore, the increased sensitivity of the assay allows for single copy gene detection in as few as 1 to 1000 cells.

The disclosed methods allow screening or detection of multiple mRNAs and small non-coding RNAs in a multiplexed format (such as detecting the same RNAs in many samples, or detecting multiple different RNAs in a single sample), for example at least 10, at least 25, at least 40, at least 50, at least 100, at least 200, at least 300, at least 400, at least 500, at least 750, at least 1000, or more RNAs in a single assay. In some embodiments, additional nucleic acids, such as genomic DNA, cDNA, tRNA, rRNA, snRNA, snoRNA, or any combination can also be detected in the described assays. In some embodiments, the disclosed methods result in capture of NPPs at spatially distinct locations, therefore the NPPs can be detected using the same detectable label and distinguished based on their position on a substrate, such as a microarray.

I. Abbreviations

FFPE formalin-fixed paraffin-embedded
miRNA microRNA
mRNA messenger RNA
NPP nuclease protection probe
piRNA piwi-interacting RNA
qNPA quantitative nuclease protection assay
siRNA small interfering RNA
snRNA small nuclear RNA
snoRNA small nucleolar RNA II. Terms Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); Robert A. Meyers (ed.), *Molecular Biology and Biotechnology: a Comprehensive Desk Reference*, published by Wiley, John & Sons, Inc., 1995 (ISBN 0471186341); and George P. Rédei, *Encyclopedic Dictionary of Genetics, Genomics, and Proteomics,* 2nd Edition, 2003 (ISBN: 0-471-26821-6).

The following explanations of terms and methods are provided to better describe the present disclosure and to guide those of ordinary skill in the art to practice the present disclosure. The singular forms "a," "an," and "the" refer to one or more than one, unless the context clearly dictates otherwise. For example, the term "comprising a cell" includes single or plural cells and is considered equivalent to the phrase "comprising at least one cell." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

All publications, patent applications, patents, and other references mentioned herein are incorporated by reference in their entirety for all purposes. All sequences associated with the GenBank Accession Nos. mentioned herein are incorporated by reference in their entirety as were present on Sep. 28, 2011, to the extent permissible by applicable rules and/or law. In case of conflict, the present specification, including explanations of terms, will control.

Although methods and materials similar or equivalent to those described herein can be used to practice or test the disclosed technology, suitable methods and materials are described below. The materials, methods, and examples are illustrative only and not intended to be limiting.

To facilitate review of the various embodiments of this disclosure, the following explanations of specific terms are provided:

Complementary: Ability to from base pairs between nucleic acids. Oligonucleotides and their analogs hybridize by hydrogen bonding, which includes Watson-Crick, Hoogsteen or reversed Hoogsteen hydrogen bonding, between complementary bases. Generally, nucleic acid molecules consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acids or two distinct regions of the same nucleic acid.

"Specifically hybridizable" and "specifically complementary" are terms that indicate a sufficient degree of complementarity such that stable and specific binding occurs between the probe (for example, an NPP) or its analog and the nucleic acid target (such as DNA or RNA target, such as mRNA or miRNA). The probe or analog need not be 100% complementary to its target sequence to be specifically hybridizable. A probe or analog is specifically hybridizable when there is a sufficient degree of complementarity to avoid non-specific binding of the probe or analog to non-target sequences under conditions where specific binding is desired, for example in the methods disclosed herein.

Conditions sufficient for: Any environment that permits the desired activity, for example, that permits specific binding or hybridization between two nucleic acid molecules (such as an NPP and a target nucleic acid or between an NPP and a bifunctional ("programming") linker) or that permits a nuclease to remove (or digest) unbound nucleic acids.

Contact: Placement in direct physical association; includes both in solid and liquid form. For example, contacting can occur in vitro with a nucleic acid probe (e.g., an NPP) and biological sample in solution.

Detect: To determine if an agent (such as a signal, particular nucleotide, amino acid, nucleic acid molecule, and/or organism) is present or absent. In some examples, this can further include quantification. For example, use of the disclosed methods and probes in particular examples permits detection of mRNA and miRNA in a sample.

Detectable label: A compound or composition that is conjugated directly or indirectly to another molecule (such as a nucleic acid molecule) to facilitate detection of that molecule. Specific, non-limiting examples of labels include fluorescent and fluorogenic moieties, chromogenic moieties, haptens, affinity tags, and radioactive isotopes. The label can be directly detectable (e.g., optically detectable) or indirectly detectable (for example, via interaction with one or more additional molecules that are in turn detectable). Exemplary labels in the context of the probes (e.g., NPPs) disclosed herein are described below. Methods for labeling nucleic acids, and guidance in the choice of labels useful for various purposes, are discussed, e.g., in Sambrook and Russell, in *Molecular Cloning: A Laboratory Manual*, 3rd Ed., Cold Spring Harbor Laboratory Press (2001) and Ausubel et al., in *Current Protocols in Molecular Biology*, Greene Publishing Associates and Wiley-Intersciences (1987, and including updates).

Hybridization: The ability of complementary single-stranded DNA, RNA, or DNA/RNA hybrids to form a duplex molecule (also referred to as a hybridization complex). Nucleic acid hybridization techniques can be used to form hybridization complexes between a nucleic acid probe, and the gene it is designed to target.

"Specifically hybridizable" and "specifically complementary" are terms that indicate a sufficient degree of complementarity such that stable and specific binding occurs between the oligonucleotide (or its analog) and the nucleic acid target (such as DNA or RNA target, such as mRNA or miRNA). The oligonucleotide or oligonucleotide analog need not be 100% complementary to its target sequence to be specifically hybridizable. Specific hybridization is also referred to herein as "specific binding."

Hybridization conditions resulting in particular degrees of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) *Molecular Cloning*, second edition, Cold Spring Harbor Laboratory, Plainview, N.Y. (chapters 9 and 11).

Nuclease: An enzyme that cleaves a phosphodiester bond. An endonuclease is an enzyme that cleaves an internal phosphodiester bond in a nucleotide chain (in contrast to exonucleases, which cleave a phosphodiester bond at the end of a nucleotide chain). Endonucleases include restriction endonucleases or other site-specific endonucleases (which cleave DNA at sequence specific sites), DNase I, Bal 31 nuclease, S1 nuclease, Mung bean nuclease, Ribonuclease A, Ribonuclease T1, RNase I, RNase PhyM, RNase U2, RNase CLB, micrococcal nuclease, and apurinic/apyrimidinic endonucleases. Exonucleases include exonuclease III and exonuclease VII. In particular examples, a nuclease is specific for single-stranded nucleic acids, such as S1 nuclease, Mung bean nuclease, Ribonuclease A, or Ribonuclease T1.

Nucleic acid: A deoxyribonucleotide or ribonucleotide polymer in either single or double stranded form, and unless otherwise limited, encompassing analogs of natural nucleotides that hybridize to nucleic acids in a manner similar to naturally occurring nucleotides. The term "nucleotide" includes, but is not limited to, a monomer that includes a base (such as a pyrimidine, purine or synthetic analogs thereof) linked to a sugar (such as ribose, deoxyribose or synthetic analogs thereof), or a base linked to an amino acid, as in a peptide nucleic acid. A nucleotide is one monomer in a polynucleotide. A nucleotide sequence refers to the sequence of bases in a polynucleotide.

A target nucleic acid (such as a target miRNA or target mRNA) is a defined region or particular portion of a nucleic acid molecule, for example a small non-coding RNA (such as an miRNA, siRNA, or piRNA) or mRNA of interest. In an example where the target nucleic acid sequence is a target miRNA or a target mRNA, such a target can be defined by its specific sequence or function; by its gene or protein name; or by any other means that uniquely identifies it from among other nucleic acids.

In some examples, alterations of a target nucleic acid sequence (e.g., an miRNA, siRNA, piRNA, or an mRNA) are "associated with" a disease or condition. That is, detection of the target nucleic acid sequence can be used to infer the status of a sample with respect to the disease or condition. For example, the target nucleic acid sequence can exist in two (or more) distinguishable forms, such that a first form correlates with absence of a disease or condition and a second (or different) form correlates with the presence of the disease or condition. The two different forms can be qualitatively distinguishable, such as by nucleotide polymorphisms or mutation, and/or the two different forms can be quantitatively distinguishable, such as by the number of copies of the target nucleic acid sequence that are present in a sample.

Probe: A nucleic acid molecule capable of hybridizing with a target nucleic acid molecule (e.g., a target small non-coding RNA (such as miRNA) or mRNA nucleic acid molecule) and, when hybridized to the target, is capable of being detected either directly or indirectly. Thus probes permit the detection, and in some examples quantification, of a target nucleic acid molecule, such as an miRNA or mRNA. In some examples, a probe includes a detectable label.

A nuclease protection probe (NPP) is a nucleic acid molecule complementary to a target small non-coding RNA or mRNA that is capable of hybridizing to the target small non-coding RNA (such as miRNA) or mRNA. The NPP protects the complementary target nucleic acid molecule from cleavage by a nuclease, such as a nuclease specific for single-stranded nucleic acids.

RNA (ribonucleic acid): RNA is a long chain polymer which consists of nucleic acids joined by 3'-5' phosphodiester bonds. The repeating units in RNA polymers are four different nucleotides, each of which comprises one of the four bases, adenine, guanine, cytosine, and uracil bound to a ribose sugar to which a phosphate group is attached. In general, DNA is transcribed to RNA by an RNA polymerase. RNA transcribed from a particular gene contains both introns and exons of the corresponding gene; this RNA is also referred to as pre-mRNA. RNA splicing subsequently removes the intron sequences and generates a messenger RNA (mRNA) molecule, which can be translated into a polypeptide. Triplets of nucleotides (referred to as codons) in an mRNA molecule code for each amino acid in a polypeptide, or for a stop signal.

Another form of RNA is small non-coding RNA, including microRNA (miRNA), which are single-stranded RNA molecules that regulate gene expression. miRNAs are generally about 18-25 nucleotides in length. microRNAs typically modulate gene expression (e.g., increase or decrease translation) by promoting cleavage of target mRNAs or by blocking translation of the cellular transcript. miRNAs are processed from primary transcripts known as pri-miRNA to short stem-loop structures called precursor (pre)-miRNA and finally to functional, mature miRNA. Mature miRNA molecules are partially complementary to one or more messenger RNA molecules, and their primary function is to down-regulate gene expression. miRNA sequences are publicly available. For example, miRBase (mirbase.org) includes a searchable database of annotated miRNA sequences. miRNA sequences are also available through other databases known to one of ordinary skill in the art, including the National Center for Biotechnology Information (ncbi.nlm.nih.gov). One of ordinary skill in the art can also identify targets for specific miRNAs utilizing public databases and algorithms, for example at MicroCosm Targets (ebi.ac.uk/enright-srv/microcosm/htdocs/targets/), TargetScan (targetscan.org), and PicTar (pictar.mdc-berlin.de).

Sample: A biological specimen containing DNA (for example, genomic DNA or cDNA), RNA (including mRNA or miRNA), protein, or combinations thereof, in some examples obtained from a subject. Examples include, but are not limited to cells, cell lysates, chromosomal preparations, peripheral blood, urine, saliva, tissue biopsy (such as a tumor biopsy or lymph node biopsy), surgical specimen, bone marrow, amniocentesis samples, and autopsy material. In one example, a sample includes RNA, such as mRNA and/or miRNA. In particular examples, samples are used directly (e.g., fresh or frozen), or can be manipulated prior to use, for example, by fixation (e.g., using formalin) and/or embedding in wax (such as FFPE tissue samples).

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene*, 73:237-44, 1988; Higgins & Sharp, *Comput. Appl. Biosci.* 5:151-3, 1989; Corpet et al., *Nucl. Acids Res.* 16:10881-90, 1988; Huang et al. *Comput. Appl. Biosci.* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100.

One indication that two nucleic acid molecules are closely related is that the two molecules hybridize to each other under stringent conditions. Stringent conditions are sequence-dependent and are different under different environmental parameters. The nucleic acid probes disclosed herein are not limited to the exact sequences shown, as one of ordinary skill in the art will appreciate that changes can be made to a sequence, and not substantially affect the ability of a probe to function as desired. For example, sequences having at least 80%, at least 85%, at least 90%, at least 91%, at least 92%, at least 93%, at least 94%, at least 95%, at least 96%, at least 97%, at least 98%, or at least 99%, such as 100% sequence identity to the disclosed probes are provided herein (e.g., SEQ ID NOS: 17-56). One of ordinary skill in the art will appreciate that these sequence identity ranges are provided for guidance only; it is possible that probes can be used that fall outside these ranges.

Simultaneous: Occurring at the same time or substantially the same time and/or occurring in the same sample or the same reaction (for example, contemporaneous). In some examples, the events occur within 1 microsecond to 120 seconds of one another (for example within 0.5 to 120 seconds, 1 to 60 seconds, or 1 to 30 seconds, or 1 to 10 seconds).

Small non-coding RNA: Any non-coding RNA of about 60 nucleotides or less. Small (or short) non-coding RNAs include microRNA (miRNA; above). Other small non-coding RNAs include small interfering RNA (siRNA), which are about 19-23 nucleotides in length. siRNAs are double-stranded nucleic acid molecules that modulate gene expression through the RNAi pathway. siRNA molecules generally have 2-nucleotide overhangs on each 3' end. However, siRNAs can also be blunt ended. Generally, one strand of a siRNA molecule is at least partially complementary to a target nucleic acid, such as a target mRNA. siRNAs are also referred to as "small inhibitory RNAs" or "short inhibitory RNAs."

Additional small non-coding RNAs include Piwi-interacting RNA (piRNA), which are about 25-30 nucleotides in length and bind Piwi proteins. piRNAs are involved in germ cell development, stem cell self-renewal, and retrotansoposon silencing. Transcription initiation RNAs (tiRNAs) are about 18 nucleotides in length. They are generally found downstream of transcriptional start sites and are involved in regulating transcription of protein-coding genes by targeting epigenetic silencing complexes. Centromere repeat associated small interacting RNA (crasiRNA) are about 34-42 nucleotides in length and are processed from longer dsRNAs. They are involved in recruitment of heterochromatin and/or centromeric proteins. Another type of small non-coding RNA is telomere-specific small RNA (tel-siRNA), which are about 24 nucleotides in length and are 2'-O-methylated at their 3' end. They are involved in epigenetic regulation.

Subject: Any multi-cellular vertebrate organism, such as human and non-human mammals (e.g., veterinary subjects). In one example, a subject is known or suspected of having a tumor.

Surface (or substrate): Any solid support or material which is insoluble, or can be made insoluble by a subsequent reaction. Numerous and varied solid supports are known to those in the art and include, without limitation, nitrocellulose, the walls of wells of a reaction tray, multi-well plates, test tubes, polystyrene beads, magnetic beads, membranes, and microparticles (such as latex particles). Any suitable porous material with sufficient porosity to allow access by detector reagents and a suitable surface affinity to immobilize capture reagents (e.g., oligonucleotides) is contemplated by this term. For example, the porous structure of nitrocellulose has excellent absorption and adsorption qualities for a wide variety of reagents, for instance, capture reagents. Nylon possesses similar characteristics and is also suitable. Microporous structures are useful, as are materials with gel structure in the hydrated state.

Further examples of useful solid supports include natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers which may be prepared with suitably porous structures, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer.

III. Methods of Detecting mRNA and Small Non-coding RNA

Disclosed herein are methods of co-detecting (such as simultaneously or concurrently detecting) mRNA and small non-coding RNA (such as miRNA, siRNA, or piRNA) in a sample, for example detecting mRNA and small non-coding RNA in the same sample or same assay (for example, in the same well of an assay plate or array). In particular embodiments, the methods include co-detecting mRNA and miRNA in a sample. In some embodiments, the methods include contacting a sample with a plurality of NPPs including at least one NPP which specifically binds to a target mRNA and at least one NPP which specifically binds to a target small non-coding RNA (such as a miRNA) under conditions sufficient for each of the NPPs to specifically bind to its target mRNA or small non-coding RNA, wherein each of the plurality of NPPs includes a detectable label. The sample is contacted with a nuclease specific for single-stranded nucleic acid molecules under conditions sufficient to remove (or digest) unbound nucleic acid molecules and then the NPP is detected. One of ordinary skill in the art will appreciate that other nucleic acid molecules can also be detected in combination with the mRNA and small non-coding RNA, including DNA (e.g., genomic DNA or cDNA) or other RNA (such as rRNA, tRNA, snRNA, or snoRNA).

Following hybridization and nuclease treatment, the NPPs remaining in the mixture can be detected by any suitable method known in the art or developed hereafter. In some examples, the NPPs are detected utilizing a capture method (for example, capture of the NPPs on an array or plurality of beads), for example, sequence-specific capture of each NPP. In other examples, the NPPs are detected by methods which do not require sequence-specific capture of the NPPs, for example by utilizing differing detectable labels on each NPP. Exemplary methods are discussed below.

In some embodiments, the sample is contacted with a surface including multiple spatially discrete regions, each of which include at least one anchor in association with a bifunctional linker including a first portion which specifically binds to the anchor and a second portion which specifically binds to one of the plurality of NPPs, under conditions sufficient for each of the plurality of NPPs to specifically bind to the second portion of a bifunctional linker. The NPP bound to the second portion of the bifunctional linker is detected utilizing the detectable label included in the NPP, thereby detecting mRNA and miRNA in the sample. The NPPs can be discriminated based on their position on the surface (for example, if one or more of the plurality of NPPs includes the same detectable label) and/or the particular detectable label detected (for example, if one or more of the plurality NPPs include different detectable labels).

In some examples, the sample is contacted with a plurality of surfaces (such as a population of beads or other particles), wherein each surface (such as each bead or sub-population of beads within a mixed bead population) includes at least one anchor in association with a bifunctional linker including a first portion which specifically binds to the anchor and a second portion which specifically binds to one of the plurality of NPPs, under conditions sufficient for each of the plurality of NPPs to specifically bind to the second portion of a bifunctional linker. The NPP bound to the second portion of the bifunctional linker is detected utilizing the detectable label included in the NPP, thereby detecting mRNA and miRNA in the sample.

In other embodiments, the sample is contacted with a surface including multiple spatially discrete regions, each of which include at least one oligonucleotide which specifically binds to one of the plurality of NPPs under conditions sufficient for each of the plurality of NPPs to bind to the oligonucleotide. The NPP bound to the oligonucleotide is detected utilizing the detectable label included in the NPP, thereby detecting mRNA and miRNA in the sample. The NPPs can be discriminated based on their position on the surface (for example, if one or more of the plurality of NPPs includes the same detectable label) and/or the particular detectable label detected (for example, if one or more of the plurality NPPs include different detectable labels).

In some examples, the sample is contacted with a plurality of surfaces (such as a population of beads or other particles), wherein each surface (such as each bead or sub-population of beads within a mixed bead population) includes at least one oligonucleotide which specifically binds to one of the plurality of NPPs, under conditions sufficient for each of the plurality of NPPs to specifically bind to the oligonucleotides. The NPP bound to the oligonucleotide is detected utilizing the detectable label included in the NPP, thereby detecting mRNA and miRNA in the sample.

The disclosed methods utilize a quantitative nuclease protection assay (qNPA), for example as described in International Patent Publications WO 99/032663; WO 00/037683; WO 00/037684; WO 00/079008; WO 03/002750; and WO 08/121,927; and U.S. Pat. Nos. 6,238, 869; 6,458,533; and 7,659,063, all of which are incorporated herein by reference in their entirety. See also, Martel et al., *Assay and Drug Development Technologies.* 2002, 1 (1-1): 61-71; Martel et al., *Progress in Biomedical Optics and Imaging,* 2002, 3:35-43; Martel et al., *Gene Cloning and Expression Technologies,* Q. Lu and M. Weiner, Eds., Eaton Publishing, Natick (2002); Seligmann *PharmacoGenomics,* 2003, 3:36-43; Martel et al., "Array Formats" in "Microarray Technologies and Applications," U. R. Muller and D. Nicolau, Eds, Springer-Verlag, Heidelberg (2005); Sawada et al., *Toxicology in Vitro,* 20:1506-1513, 2006; Bakir, et al., *Bioorg. & Med. Chem. Lett,* 17:3473-3479, 2007; Kris et al., *Plant Physiol.* 144:1256-1266, 2007; Roberts et al., *Laboratory Investigation,* 87:979-997, 2007; Rimsza et al., *Blood,* 2008 Oct. 15, 112 (8):3425-3433; Pechhold et al., *Nature Biotechnology,* 27:1038-1042, 2009. All of these are fully incorporated by reference herein. The disclosed methods include modifications to the qNPA conditions and NPPs that unexpectedly permit simultaneous detection (for example in the same qNPA reaction or assay) of mRNA and small non-coding RNA (e.g., miRNA). FIG. 1 is a schematic diagram showing an exemplary method of simultaneously detecting mRNA and miRNA in a sample by qNPA.

In some embodiments, the methods can include contacting a sample (such as a sample including nucleic acids, such as RNAs) with plurality of NPPs including at least one NPP which specifically binds to a target mRNA and at least one NPP which specifically binds to a target miRNA (or other target small non-coding RNA). The plurality of NPPs includes at least one (such as at least 1, 2, 3, 4, 5, 10, 15, 20, 25, 50, 75, 100, 200, 300, 500, 1000, 2000, 3000, or more) NPPs which each specifically bind to a target mRNA and at least one (such as at least 1, 2, 3, 4, 5, 10, 15, 20, 25, 50, 75, 100, 200, 300, 500, 1000, 2000, 3000, or more) NPPs which each specifically bind to a target miRNA. In some examples, the plurality of NPPs include 2 to 5000 (such as 2 to 3000, 10 to 1000, 50 to 500, 25 to 300, 50 to 300, 10 to 100, or 50 to 100) NPPs. In particular examples, the plurality of NPPs includes 47 or 188 NPPs. The plurality of NPPs can include any combination of NPPs specific for mRNAs and miRNAs. In some examples, the plurality of NPPs includes more than one (such as 2, 3, 4, 5, or more) different NPPs specific for a single target mRNA or miRNA. The plurality of NPPs are incubated with the sample under conditions sufficient for the NPPs to specifically hybridize to their respective target mRNA or miRNA (and in some examples to additional nucleic acids). The sample is contacted with a nuclease specific for single-stranded nucleic acids (for example, S1 nuclease), and the presence of the each NPP is detected. The mRNA(s) and miRNA(s) are identified as present in the sample when their respective NPP is detected.

Disclosed herein are conditions sufficient for a plurality of NPPs to specifically and simultaneously hybridize (for example in the same reaction) to target mRNAs and miRNAs, such as mRNAs and miRNAs present in a sample (such as a sample from a subject). For example, the features (such as length, base composition, and degree of complementarity) that will enable a nucleic acid (e.g., an NPP) to hybridize to another nucleic acid (e.g., a target mRNA or target miRNA) under conditions of selected stringency, while minimizing non-specific hybridization to other substances or molecules can be determined based on the present disclosure. Characteristics of the NPPs are discussed in more detail in Section IV, below. Typically, the nucleic acid sequence of an NPP will have sufficient complementarity to its corresponding target mRNA or target miRNA to enable it to hybridize under selected stringent hybridization conditions, for example hybridization at about 37° C. or higher (such as about 37° C., 42° C., 50° C., 55° C., 60° C., 65° C., 70° C., 75° C., or higher). Among the hybridization reaction parameters which can be varied are salt concentration, buffer, pH, temperature, time of incubation, amount and type of denaturant such as formamide. For example, nucleic acid (e.g., a plurality of NPPs) can be added to a sample at a concentration ranging from about 10 pM to about 10 nM (such as about 30 pM to 5 nM, about 100 pM to about 1 nM), in a buffer such as, for example, 6×SSPE-T (0.9 M NaCl, 60 mM $NaH_2PO_4$, 6 mM EDTA, and 0.05% Triton X-100) or lysis buffer (described below). In one example, each NPP is added to the sample at a final concentration of at least 10 pM, such as at least 20 pM, at least 30 pM, at least 50 pM, at least 100 pM, at least 150 pM, at least 200 pM, at least 500 pM, at least 1 nM, or at least 10 nM. In one example, each NPP is added to the sample at a final concentration of about 30 pM. In another example, each NPP is added to the sample at a final concentration of about 167 pM. In a further example, each NPP is added to the sample at a final concentration of about 1 nM.

The nucleic acids in the sample are denatured (for example at about 95° C. to about 105° C. for about 5-15 minutes) and hybridized to the plurality of NPPs for between about 10 minutes and about 72 hours (for example, at least about 1 hour to 48 hours, about 6 hours to 24 hours, about 12 hours to 18 hours, or overnight) at a temperature ranging from about 4° C. to about 70° C. (for example, about 37° C. to about 65° C., about 42° C. to about 60° C., or about 50° C. to about 60° C.). In some examples, the plurality of NPPs is incubated with the sample at a temperature of at least about 37° C., at least about 40° C., at least about 45° C., at least about 50° C., at least about 55° C., at least about 60° C., at least about 65° C., or at least about 70° C. In one example, the plurality of NPPs is incubated with the sample at about 37° C. In another example, the plurality of NPPs is incubated with the sample at about 42° C. In a further example, the plurality of NPPs is incubated with the sample at about 50° C.

In some embodiments, the methods do not include nucleic acid purification (for example, nucleic acid purification is not performed prior to contacting the sample with the NPPs and/or nucleic acid purification is not performed following contacting the sample with the NPPs). In some examples, the methods do not include nucleic acid amplification (for example, nucleic acid amplification is not performed prior to contacting the sample with the NPPs and/or nucleic acid amplification is not performed following contacting the sample with the NPPs). In some examples, no pre-processing of the sample is required except for cell lysis. In some examples, cell lysis and contacting the sample with the plurality of NPPs occur sequentially. In other examples, cell lysis and contacting the sample with the plurality of NPPs occur concurrently, in some non-limiting examples without any intervening steps. However, in some examples, the disclosed methods can include nucleic acid purification, nucleic acid amplification, and/or pre-processing of the sample (for example in addition to cell lysis).

Following hybridization of the NPPs and nucleic acids in the sample, the sample is subjected to a nuclease protection procedure. NPPs which have hybridized to a target mRNA or target non-coding RNA (such as a target miRNA) are not hydrolyzed by the nuclease and can be subsequently detected.

Treatment with one or more nucleases will destroy nucleic acid molecules other than the NPPs that have hybridized to a target mRNA or target small non-coding RNA present in the sample. For example, if the sample includes a cellular extract or lysate, unwanted nucleic acids, such as genomic DNA, cDNA, tRNA, rRNA, mRNA, and miRNA other than the target mRNAs and small non-coding RNAs of interest and portions of the target mRNA or small non-coding RNAs of interest that are not hybridized to complementary NPP sequences, can be substantially destroyed in this step. Any of a variety of nucleases can be used, including, pancreatic RNAse, mung bean nuclease, S1 nuclease, RNAse A, Ribonuclease T1, Exonuclease III, Exonuclease VII, RNAse CLB, RNAse PhyM, RNAse U2, or the like, depending on the nature of the hybridized complexes and of the undesirable nucleic acids present in the sample. One of ordinary skill in the art can select an appropriate nuclease. In a particular example, the nuclease is specific for single-stranded nucleic acids, for example S1 nuclease. An advantage of using a nuclease specific for single-stranded nucleic acids in some method embodiments disclosed herein is to remove such single-stranded ("sticky") molecules from subsequent reaction steps where they may lead to undesirable background or cross-reactivity. S1 nuclease is commercially available from for example, Promega, Madison, Wis. (cat. no. M5761); Life Technologies/Invitrogen, Carlsbad, Calif. (cat. no. 18001-016); Fermentas, Glen Burnie, Md. (cat. no. EN0321), and others. Reaction conditions for these enzymes are well-known in the art and can be optimized empirically.

In some examples, S1 nuclease diluted in an appropriate buffer (such as 0.25 M sodium acetate, pH 4.5, 1.4 M NaCl, 0.0225 M $ZnSO_4$, 0.05% KATHON) is added to the hybridized probe/sample mixture and incubated at about 37° C. to about 50° C. (such as about 37° C.) for about 30-120 minutes (for example, about 60-90 minutes or about 120 minutes) to digest non-hybridized nucleic acid and NPPs.

The samples can optionally be treated to otherwise remove non-hybridized material and/or to inactivate or remove residual enzymes (e.g., by phenol extraction, precipitation, column filtration, etc.). In some examples, the samples are optionally treated to dissociate the target nucleic acid (such as target mRNA or target miRNA) from its complementary NPP (e.g., using base hydrolysis and heat). After hybridization, the hybridized target can be degraded, e.g., by nucleases or by chemical treatments, leaving the NPP in direct proportion to how much probe had been hybridized to target. Alternatively, the sample can be treated so as to leave the (single strand) hybridized portion of the target, or the duplex formed by the hybridized target and the probe, to be further analyzed.

The NPPs are detected by any suitable means, based upon the detectable label present on the NPPs. In a specific, non-limiting example, the NPPs include a biotin label. In this example, the NPPs can be detected by incubating the sample (such as support, e.g., array or bead) with avidin-HRP or streptavidin-HRP and then contacting the sample with a chromogenic or chemiluminescent substrate. In one non-limiting example, the substrate is TMA-3 (Lumigen, Southfield, Mich.). Additional chemiluminescent substrates are commercially available, such as LUMIGLO (KPL, Gaithersburg, Md.), SUPERSIGNAL (Pierce, Rockford, Ill.), and ECL (Amersham/GE Healthcare, Piscataway, N.J.). Signal produced by the substrate is detected, for example utilizing a microarray imager (such as an OMIX, OMIX HD, CAPELLA, or SUPERCAPELLA imager; HTG Molecular Diagnostics, Tucson, Ariz.). In another example, the NPPs include a fluorescent label, such as Cy-3 or Cy-5. The NPPs can be detected utilizing a standard microarray imager (such as a TYPHOON imager (GE Life Sciences, Piscataway, N.J.), a GENEPIX microarray scanner (Molecular Devices, Sunnyvale, Calif.), or GENECHIP scanner (Affymetrix, Santa Clara, Calif.)), flow cytometry methods, or fluorescent microscopy methods. One of ordinary skill in the art can select suitable detection methods and reagents for these or other detectable labels.

In some embodiments, the detection method includes one or more positive and/or negative controls subject to the same reaction conditions as the actual experimental NPPs. In some examples, a "positive control" includes an internal normalization control for variables such as the number of cells lysed for each sample, the recovery of RNA, or the hybridization efficiency, such as one or more NPPs (and in some examples, corresponding linkers) which are specific for one or more basal level or constitutive housekeeping genes, such as structural genes (e.g., actin, tubulin, or others) or DNA binding proteins (e.g., transcription regulation factors, or others). In some examples, a positive control includes glyceraldehyde-3-phosphate dehydrogenase (GAPDH), peptidylproylyl isomerase A (PPIA), large ribosomal protein (RPLP0), ribosomal protein L19 (RPL19), or other housekeeping genes discussed below. In other examples, a positive control includes an NPP specific for an RNA that is not found in the sample (for example an RNA sequence not found in nature or one not present in the sample, such as an RNA sequence from a species other than that being tested, e.g., a plant RNA sequence when human nucleic acids are being analyzed). The corresponding RNA (such as in vitro transcribed RNA or RNA isolated from an unrelated sample) is added to the sample prior to hybridization with the plurality of NPPs. Alternatively, the positive control NPP is added to the sample after nuclease treatment, making addition of RNA to the sample unnecessary. In some examples, a "negative control" includes one or more NPPs and corresponding linkers that are known not to be expressed in the sample, for example as a control for hybridization specificity, such as an RNA not found in nature or an RNA from another species (for example, *Arabidopsis thaliana* AP2-like ethylene-responsive transcription factor (ANT)).

In some embodiments, the signal from each NPP is normalized to the signal of at least one housekeeping mRNA, for example to account for differences in cellularity between samples. Exemplary housekeeping genes include one or more of GAPDH (glyceraldehyde 3-phosphate dehydrogenase), SDHA (succinate dehydrogenase), HPRT1 (hypoxanthine phosphoribosyl transferase 1), HBS1L (HBS1-like protein), β-actin (ACTB), β-2 microglobulin (B2m), and AHSP (alpha hemoglobin stabilizing protein). One of ordinary skill in the art can select additional housekeeping genes for use in normalizing signals in the disclosed assays, including, but not limited to ribosomal protein S13 (RPS13), ribosomal protein S20 (RPS20), ribosomal protein L27 (RPL27), ribosomal protein L37 (RPL37), ribosomal protein 38 (RPL38), ornithine decarboxylase antizyme 1 (OAZ1), polymerase (RNA) II (DNA directed) polypeptide A, 220 kDa (POLR2A), yes-associated protein 1 (YAP1), esterase D (ESD), proteasome (prosome, macropain) 26S subunit, ATPase, 1 (PSMC1), eukaryotic translation initiation factor 3, subunit A (EIF3A), or 18S rRNA (see, e.g., de Jonge et al., *PLoS One* 2:e898, 2007; Saviozzi et al., *BMC Cancer* 6:200, 2006; Kouadjo et al., *BMC Genomics* 8:127, 2007; each of which is incorporated herein by reference). The normalized values can be directly compared between samples or assays (for example, between two different samples in a single assay or between the same sample tested in two separate assays).

A. Detection of NPPs Utilizing Anchors and Programming Linkers

In some embodiments, following hybridization and nuclease treatment, the sample is contacted with a surface that includes multiple spatially discrete regions, each including at least one anchor associated with a bifunctional linker (also referred to as a "programming linker"). Alternatively, following hybridization and nuclease treatment, the sample is contacted with a plurality of surfaces, wherein each includes at least one anchor associated with a bifunctional linker. For example, the plurality of surfaces can be a population of beads, wherein subpopulations of the beads each include at least one anchor associated with a bifunctional linker. For example a first subpopulation could include at least one anchor associated with a first bifunctional linker, while a second subpopulation could include at least one different anchor associated with a second bifunctional linker, and so on. In another example, the surface can be a flow cell, such as a flow cell with a plurality of channels, wherein subpopulations of the channels each include at least one anchor associated with a bifunctional linker. For example a first subpopulation could include at least one anchor associated with a first bifunctional linker, while a second subpopulation could include at least one different anchor associated with a second bifunctional linker, and so on.

The anchor and the bifunctional linker are associated by hybridization, annealing, covalent linkage, or other binding. The bifunctional linker includes a first portion which specifically binds to (for example, is complementary to) the anchor and a second portion which specifically binds to (for example, is complementary to) one of the plurality of NPPs. In some examples, the sample is treated to inactivate the nuclease (for example, incubating at 95° C. for 15-30 minutes) and neutralized prior to contacting with the surface. The sample is incubated with the surface (for example, an array) for a sufficient period of time for the NPPs to specifically bind (for example, hybridize) to the bifunctional linkers associated with the anchors. In some examples, the incubation of the sample with the surface at about 37° C. to about 65° C. (for example, about 45° C. to about 60° C., or about 50° C. to about 60° C., such as 50° C.) for about 12 to 36 hours (for example about 12 to 24 hours, such as about 16 to 24 hours, or overnight) to allow NPP hybridization to the bifunctional linker ("NPP capture").

In some embodiments, the disclosed methods include an anchor on a surface (for example on an array, bead, or flow cell), which is associated with a bifunctional linker which is utilized to capture the NPP following the nuclease step. In some examples, an anchor is an oligonucleotide of about 8 to 150 nucleotides in length (for example, about 15 to 100, 20 to 80, 25 to 75, or 25 to 50, such as about 15, 20, 25, 30, 35, 40, 45, 50, 55, 60, 65, 70, 75, 80, 85, 90, 95, 100, 110, 120, 130, 140, or 150 nucleotides). In one non-limiting example, the anchor is about 25 nucleotides in length. In some examples, the anchor includes a first portion that specifically binds to the first portion of the bifunctional linker and a second portion that acts as a spacer between the surface and the first portion of the anchor. In some examples, the second portion of the anchor is about 6 to 60 carbon atoms or nucleotides in length (such as about 6, 12, 24, 30, 36, 42, 48, 54, or 60 carbon atoms or nucleotides). In other examples, the second portion of the anchor is about 5 to 100 carbon atoms or nucleotides in length (such as about 10 to 50, 15 to 40, 20 to 30, or about 25 carbon atoms or nucleotides).

The base composition for anchors of the disclosed methods is such that the thermodynamic stability of the anchor and bifunctional linker pairing is high. In some examples, the percentage base composition for the anchors is about 30-40% G, 30-40% C, 10-20% A, and 10-20% T. In some examples, nearest neighbor frequency in the anchors minimizes G-G or C-C nearest neighbors to reduce side reactions mediated via G-quartet formation.

Methods of designing and synthesizing anchors of use in the disclosed methods are described, e.g., in PCT Publication No. WO 97/029736 (PCT/US1997/024098), incorporated herein by reference. In some examples, a set of anchors which are substantially dissimilar from one other is desirable. An exemplary algorithm for obtaining a set of dissimilar anchors is as follows:

1) The set size is defined. In some embodiments, 16, 24, 36, 48, 49, 64, 81, 96, and 100 constitute useful sizes.

2) The overall sequence structure of the anchor set is defined. The length and base composition as described above are used to define such parameters. In general, the number of G bases and C bases are held equal as are the number of A bases and T bases. This equality optimizes the configurational diversity of the final sets. Thus, such sets will be described by the equation $G_n C_n A_m T_m$.

3) For a set structure defined by m and n, a random number generator is employed to produce a set of random sequence isomers.

4) One member of the random sequence set is selected to be used as element #1 of the set.

5) The maximum similarity allowable among set members is defined. Similarity is defined in terms of local pair-wise base comparison. For example, when two oligomer strands of identical length n are aligned such that 5' and 3' ends are in register, the lack of mismatches refers to the situation where at all positions 1-n, bases in the two strands are identical. Complete mismatching refers to the situation wherein at all positions 1-n, bases in the two strands are different. For example, a useful maximum similarity might be 10 or more mismatches within a set of 16, 16mer capture probes.

6) A second member of the random sequence set is selected and its similarity to element #1 is determined. If element #2 possesses less than the maximum allowable similarity to element #1, it will be kept in the set. If element #2 possesses greater than the maximum allowable similarity, it is discarded and a new sequence is chosen for comparison. This process is repeated until a second element has been determined.

7) In a sequential manner, additional members of the random sequence set are chosen which satisfy the dissimilarity constraints with respect to all previously selected elements.

One non-limiting example of a set of 16 anchors which can be utilized in the disclosed methods is shown in Table 1.

TABLE 1

Exemplary anchor sequences

| Anchor Sequence (5'->3') | SEQ ID NO: |
|---|---|
| TGATTCAGACCGGCCG | 1 |
| CCCGGGGCGTCTTAAC | 2 |
| GGACGCCATATGCGCT | 3 |
| TGAGGGCTCCGCCATA | 4 |
| AACCCGTGACGTGTGC | 5 |
| AGCATCGCCGGTCCTG | 6 |
| CCTGCAAGGCTGACGT | 7 |
| CAGTTGTCGACCCCGG | 8 |
| CGGCGCGTCCAATTCG | 9 |
| ATCGATCTGAGGGCCC | 10 |
| GTACATGCGGCCTGCA | 11 |
| TAGCCGCTCGCTAGAG | 12 |
| CCTAGTGATGACCGGC | 13 |
| GTCTGAGGGCAACCTC | 14 |
| CTAGCTGGCTACGCAG | 15 |
| GCCATCCGCTTGGAGC | 16 |

Some of the surfaces (or substrates) which can be used in the disclosed methods are readily available from commercial suppliers. In some embodiments, the surface is a 96-, 384-, or 1536-well microtiter plate, such as modified plates sold by Corning Costar (Tewksbury, Mass.). In other embodiments, a substrate includes one or more beads (such as a population of beads that can be differentiated by size or color, for example by flow cytometry). Alternatively, a surface comprising wells which, in turn, comprise indentations or "dimples" can be formed by micromachining a substance such as aluminum or steel to prepare a mold, then microinjecting plastic or a similar material into the mold to form a structure. Alternatively, a structure comprised of glass, plastic, ceramic, or the like, can be assembled. The separator can be, for example, a piece of material, e.g., silicone, with holes spaced throughout, so that each hole will form the walls of a test well when the three pieces are joined. The subdivider can be, for example, a thin piece of material, e.g., silicone, shaped in the form of a screen or fine meshwork. In some examples, the base is a flat piece of material (for example glass or plastic), in, for example, the shape of the lower portion of a typical microplate used for a biochemical assay. The top surface of the base can be flat, or can be formed with indentations that will align with the subdivider shape to provide full subdivisions, or wells, within each sample well. The three pieces can be joined by standard procedures, for example the procedures used in the assembly of silicon wafers.

Suitable materials for the surface include, but are not limited to: glass, silica, gold, silver, a gel or polymer, nitrocellulose, polypropylene, polyethylene, polybutylene, polyisobutylene, polybutadiene, polyisoprene, polyvinylpyrrolidine, polytetrafluoroethylene, polyvinylidene difluoroide, polyfluoroethylene-propylene, polyethylenevinyl alcohol, polymethylpentene, polycholorotrifluoroethylene, polysulformes, hydroxylated biaxially oriented polypropylene, aminated biaxially oriented polypropylene, thiolated biaxially oriented polypropylene, ethyleneacrylic acid, thylene methacrylic acid, and blends of copolymers thereof (see U.S. Pat. No. 5,985,567).

In general, suitable characteristics of the material that can be used to form the surface include: being amenable to surface activation such that upon activation, the surface of the support is capable of covalently attaching a biomolecule such as an oligonucleotide thereto; amenability to "in situ" synthesis of biomolecules; being chemically inert such that at the areas on the support not occupied by oligonucleotides or proteins are not amenable to non-specific binding, or when non-specific binding occurs, such materials can be readily removed from the surface without removing the oligonucleotides or proteins.

A wide variety of array formats for arrangement of the anchors can be employed in accordance with the present disclosure. One suitable format includes a two-dimensional pattern of discrete cells (such as 4096 squares in a 64 by 64 array). As is appreciated by one of ordinary skill in the art, other array formats including, but not limited to slot (rectangular) and circular arrays are equally suitable for use (see U.S. Pat. No. 5,981,185). In some examples, the array is a multi-well plate.

Oligonucleotide anchors, bifunctional linkers, NPPs, or other oligonucleotides can be synthesized by conventional technology, for example, with a commercial oligonucleotide synthesizer and/or by ligating together subfragments that have been so synthesized. Nucleic acids which are too long to be reliably synthesized by such methods can be generated by amplification procedures, using conventional procedures.

In one embodiment, preformed nucleic acid anchors, such as oligonucleotide anchors, can be situated on or within the surface of a test region by any of a variety of conventional techniques, including photolithographic or silkscreen chemical attachment, disposition by ink jet technology, capillary, screen or fluid channel chip, electrochemical patterning using electrode arrays, contacting with a pin or quill, or denaturation followed by baking or UV-irradiating onto filters (see, e.g., Rava et al. (1996). U.S. Pat. No. 5,545,531; Fodor et al. (1996). U.S. Pat. No. 5,510,270; Zanzucchi et al. (1997). U.S. Pat. No. 5,643,738; Brennan (1995). U.S. Pat. No. 5,474,796; PCT WO 92/10092; PCT WO 90/15070). Anchors can be placed on top of the surface of a test region or can be, for example in the case of a polyacrylamide gel pad, imbedded within the surface in such a manner that some of the anchor protrudes from the surface and is available for interactions with a linker. In one embodiment, preformed oligonucleotide anchors are derivatized at the 5' end with a free amino group; dissolved at a concentration routinely determined empirically (e.g., about 1 μM) in a buffer such as 50 mM phosphate buffer, pH 8.5 and 1 mM EDTA; and distributed with a nanojet dispenser in droplets of about 10.4 nanoliters onto specific locations within a test well whose upper surface is that of a fresh, dry DNA BIND plate (Corning, Tewksbury, Mass.). Depending on the relative rate of oligonucleotide attachment and evaporation, it may be required to control the humidity in the wells during preparation. In another embodiment, oligonucleotide anchors can be synthesized directly on the surface of a test region, using conventional methods such as, for example, light-activated deprotection of growing oligonucleotide chains (for example, in conjunction with the use of a site directing "mask") or by patterned dispensing of nanoliter droplets of deactivating compound using a nanojet dispenser. Deprotection of all growing oligonucleotides that are to receive a single nucleotide can be done, for example, and the nucleotide then added across the surface. In another embodiment, oligonucleotide anchors are attached to the surface via the 3' ends of the oligonucleotides, using conventional methodology.

B. Detection of NPPs Utilizing Alternative Methods

In some embodiments, following hybridization and nuclease treatment the NPPs in the sample are detected utilizing alternative methods, such as high-throughput platforms. In some examples, NPPs are detected utilizing gel electrophoresis, chromatography, mass spectrometry, sequencing, conventional microarray analysis, PCR (or other amplification), or hybrid capture. In some embodiments, the NPP does not include a detectable label and indirect detection methods are utilized. Such methods are known to one of ordinary skill in the art and include, but are not limited to, those described below.

In one example, NPPs are detected utilizing a bead-based assay, such as a bead array. One example of a bead-based assay utilizes XMAP beads (Luminex, Austin, Tex.), such as a QBEAD assay. In some examples, the NPPs are captured on XMAP beads or other beads by hybridization to an oligonucleotide associated with the beads (for example for about 1-24 hours at about 50° C.). The detectable label included in the NPPs can be detected, for example by flow cytometry or related methods (such as utilizing a LUMINEX 200, FLEXMAP 3D, or other suitable instrument).

In another example, NPPs are detected utilizing a standard microarray. One example of such an array is a Nimblegen microarray (Nimblegen, Madison, Wis.). In some examples, the NPPs are hybridized to an array including oligonucleotides that specifically bind to the NPPs. The detectable label included in the NPPs can be detected.

In further examples, NPPs are detected with a "bar code" assay. One example of such as assay is NCOUNTER Analysis System (Nanostring Technologies, Seattle, Wash.). In some examples, following hybridization and nuclease treatment, the NPPs are hybridized to a probe including one or more color coded tags (a "bar-code"). Detection of the color coded tags provides identification of the NPPs included in the sample. See, e.g., WO 07/076,1282; WO 07/076,129; WO 07/139,766.

In another example, NPPs are detected using flow cell technology. Exemplary flow cells are available from Advanced Biosensor Technology (Richmond, Va.). In some examples, following hybridization and nuclease treatment, the NPPs are hybridized to corresponding oligonucleotides or bifunctional linkers (for example, complementary to at least a portion of the NPPs) in the channel of a flow cell. The presence of the NPPs can then be detected using routine methods, such as detection of a label (such as a fluorescent label), electrochemical detection, HPLC, or mass spectrometry.

In other examples, NPPs are detected by mass spectrometry. For example, mass spectrometry can be used to detect and differentiate NPPs based on their size and/or sequence composition. In still further examples, NPPs (or the region of the target hybridized to the NPP) are detected by sequencing (for example Sanger sequencing, pyrosequencing, reversible dye-terminator sequencing (Illumina sequencing), sequencing by ligation (SOLiD sequencing), semiconductor based sequencing, HELIOSCOPE sequencing, single molecule sequencing, or nanopore sequencing). In some examples, the NPPs include one or more flanking sequences at the 5'-end and/or 3'-end of the NPP. The flanking sequence(s) includes several contiguous nucleotides having a sequence (such as a sequence of at least 12 nucleotides) not found in a nucleic acid molecule present in the sample, and provide a universal hybridization and/or amplification sequence, which can also be utilized as a universal primer for sequencing of the NPP. This universal hybridization and/or amplification sequence, when having a sequence complementary to at least a portion of an amplification primer, permits multiplexing, as the same amplification primers can be used to amplify NPPs specific for different target nucleic acid molecules. In still further examples, NPPs are detected by ESENSOR technology (GenMark Diagnostics, Carlsbad, Calif.).

In some embodiments of the disclosed methods, at least two NPPs utilized in the methods include a different detectable label (such as those discussed in Section IV(A), below). The presence of a different detectable label in each NPP allows detection of the presence of label (and thus NPP). In some embodiments, the NPPs utilized in the methods are each labeled with a different hapten (such as biotin, digoxigenin, fluorescein, or dinitrophenyl). Following nuclease treatment, the presence and/or amount of each NPP can be determined by detecting each of the labels. In some examples, each label is detected by a suitable colorimetric assay, wherein presence of each label results in production of a different color product. In one non-limiting example, at least one NPP is labeled with biotin and can be detected by contacting the biotin-labeled NPP with avidin or streptavidin conjugated to horseradish peroxidase and at least one NPP is labeled with digoxigenin and can be detected by contacting the digoxigenin-labeled NPP with an anti-digoxigenin antibody conjugated to alkaline phosphatase. Presence and/or amount of the biotin-labeled NPP(s) is determined by conversion of a chromogenic substrate (such as TMB, DAB, or ABTS) by horseradish peroxidase into a colored product (for example, a blue product). Presence and/or amount of the digoxigenin-labeled NPP(s) is detected by conversion of a chromogenic substrate by alkaline phosphatase into a different colored product (such as a red product). One of ordinary skill in the art can select appropriate combinations of labels, enzymes, and substrates to detect and differentiate multiple differently labeled NPPs present in a mixture.

In other embodiments, at least two NPPs utilized in the methods are each labeled with a different fluorescent label. The presence and/or amount of each NPP remaining following nuclease treatment can be determined by detecting the fluorescent label(s) remaining in the mixture. Any method of detecting and discriminating fluorescent labels now known or developed in the future can be used. In some examples, following nuclease digestion, the mixture is separated by electrophoresis (such as capillary electrophoresis) and the fluorescent labels are detected, for example utilizing laser-induced fluorescence detection. Suitable electrophoresis and detection systems are commercially available, for example Applied Biosystems 3130 Genetic Analyzer or 3730 DNA Analyzer (Applied Biosystems, Carlsbad, Calif.). In other examples, the NPPs are captured by sequence-based methods (such as those described above) and are differentiated by the specific emission wavelength of their different fluorescent labels.

In further embodiments, NPPs are labeled with a donor fluorophore and an acceptor fluorophore, where the combination of donor and acceptor fluorophores is different for at least two of the NPPs. If the NPP does not hybridize to a target RNA, the acceptor fluorophore will be removed by the nuclease and signal will not be detected (or reduced signal will be detected). If the NPP hybridizes to a target RNA, the acceptor fluorophore will be protected from the nuclease and signal will be detected. In other examples, the acceptor fluorophore is a quencher. If the NPP does not hybridize to a target RNA, the quencher will be removed by the nuclease, and signal from the donor fluorophore will be detected. If the NPP does hybridize to a target RNA, the quencher will be protected from the nuclease and signal from the donor fluorophore will not be detected.

Additional methods of detecting differently labeled NPPs include flow cytometry. For example, NPPs labeled with different fluorescent labels can be captured on beads and differentiated by their emission spectra on flow cytometry.

IV. Nuclease Protection Probes (NPPS)

In some embodiments, the disclosed methods include co-detecting (such as simultaneously detecting) mRNA and small non-coding RNA in a sample, such as one or more target miRNAs and one or more target mRNAs. Based on the target small non-coding RNA (such as miRNA) or mRNA, NPPs can be designed for use in the disclosed methods using the criteria set forth herein in combination with the knowledge of one of ordinary skill in the art.

Factors that affect probe-target hybridization specificity include probe length, melting temperature, self-complementarity, and the presence of repetitive or non-unique sequence. See, e.g., Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999.

The specificity of a probe increases with length. Thus for example, a probe that includes 25 consecutive nucleotides will anneal to a target sequence with a higher specificity than a corresponding probe of only 15 nucleotides. Thus, the NPPs disclosed herein can be selected to include at least 10, at least 15, at least 20, at least 25, or more consecutive nucleotides complementary to a particular nucleic acid molecule (such as about 6 to 50, 10 to 40, 15 to 30, 18 to 23, 19 to 22, or 20 to 25 consecutive nucleotides complementary to a target miRNA or a target mRNA). Particular lengths of NPPs that can be used to practice the methods of the present disclosure include NPPs having at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 contiguous nucleotides complementary to a nucleic acid molecule, for example a target small non-coding RNA or target mRNA. In a particular non-limiting example, a target miRNA NPP is 18 to 23 nucleotides (such as 18, 19, 20, 21, 22, or 23 nucleotides) in length. In another non-limiting example, a target mRNA NPP is 15 to 30 nucleotides (such as 15, 16, 17, 18, 19, 20, 21, 22, 23, 24, 25, 26, 27, 28, 29, or 30 nucleotides) in length.

Conditions resulting in particular degrees of hybridization (stringency) will vary depending upon the nature of the hybridization method and the composition and length of the hybridizing nucleic acid sequences. Generally, the temperature of hybridization and the ionic strength (such as the Na$^+$ concentration) of the hybridization buffer will determine the stringency of hybridization. In some examples, the probes utilized in the disclosed methods have a melting temperature ($T_m$) of at least about 37° C., at least about 42° C., at least about 45° C., at least about 50° C., at least about 55° C., at least about 60° C., at least about 65° C., at least about 70° C., at least about 75° C., at least about 80° C., such as about 42° C.-80° C. (for example, about 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80° C.). In one non-limiting example, the probes utilized in the disclosed methods have a $T_m$ of about 42° C. Methods of calculating the $T_m$ of a probe are known to one of ordinary skill in the art (see e.g., Sambrook et al., *Molecular Cloning: A Laboratory Manual*, 3d ed., Cold Spring Harbor Press, 2001, Chapter 10). In some examples, the NPPs for mRNAs and miRNAs are selected to each have the same or a similar $T_m$ in order to facilitate simultaneous detection of mRNA and miRNA in a sample.

Also provided are probes that are degenerate at one or more positions (such as 1, 2, 3, 4, 5, or more positions), for example, a NPP that includes a mixture of nucleotides (such as 2, 3, or 4 nucleotides) at a specified position in the NPP. In some examples, the probes disclosed herein include one or more synthetic bases or alternative bases (such as inosine). In other examples, the probes disclosed herein include one or more modified nucleotides or nucleic acid analogs, such as one or more locked nucleic acids (see, e.g., U.S. Pat. No. 6,794,499) or one or more peptide nucleic acids. Modified nucleotides, unnatural nucleotides, synthetic, or alternative nucleotides can be used in mRNA NPPs and/or small non-coding RNA NPPs (such as miRNA NPPs) at one or more positions (such as 1, 2, 3, 4, 5, or more positions). In one example, an miRNA NPP includes one or more of such nucleotides. In another example, an mRNA NPP includes one or more of such nucleotides. In some examples, use of one or more modified or unnatural nucleotides in the probe can increase the $T_m$ of the probe relative to the $T_m$ of a probe of the same length and composition which does not include the modified nucleic acid. One of ordinary skill in the art can design probes including such modified nucleotides to obtain a probe with a desired $T_m$.

A. Detectable Labels

In some examples, the disclosed NPPs include one or more detectable labels, although a detectable label is not necessarily included in NPPs utilized in the disclosed methods. Detectable labels are well known in the art. A "detectable label" is a molecule or material that can be used to produce a detectable signal that indicates the presence or concentration of the NPP (e.g., the bound or hybridized probe) in a sample. Thus, a labeled nucleic acid molecule provides an indicator of the presence or concentration of a target nucleic acid sequence (e.g., a target mRNA or a target miRNA) in a sample. The disclosure is not limited to the use of particular labels, although examples are provided.

In some examples, each of the NPPs included in a plurality of NPPs utilized in the disclosed methods are labeled with the same detectable label. In other examples at least one NPP is labeled with a different detectable label than at least one other NPP in the plurality of NPPs. For example, at least one NPP included in the plurality of NPPs can be labeled with a fluorophore (such as Cy-3) and at least one NPP included in the plurality of NPPs can be labeled with a different fluorophore (such as Cy-5). In some examples, the plurality of NPPs can include at least 2, 3, 4, 5, 6, 7, 8, 9, 10, or more different detectable labels.

A label associated with one or more nucleic acid molecules (such as an NPP) can be detected either directly or indirectly. A label can be detected by any known or yet to be discovered mechanism including absorption, emission and/or scattering of a photon (including radio frequency, microwave frequency, infrared frequency, visible frequency and ultra-violet frequency photons). Detectable labels include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens, and paramagnetic and magnetic molecules or materials. Additional detectable labels include Raman (light scattering) labels (e.g., NANOPLEX biotags, Oxonica, Bucks, UK).

In non-limiting examples, NPPs are labeled with dNTPs covalently attached to hapten molecules (such as a nitroaromatic compound (e.g., dinitrophenyl (DNP)), biotin, fluorescein, digoxigenin, etc.). Methods for conjugating haptens and other labels to dNTPs (e.g., to facilitate incorporation into labeled probes) are well known in the art. For examples of procedures, see, e.g., U.S. Pat. Nos. 5,258,507, 4,772,691, 5,328,824, and 4,711,955. A label can be directly or indirectly attached to a dNTP at any location on the dNTP, such as a phosphate (e.g., α, β or γ phosphate) or a sugar. In some examples, detection of labeled nucleic acid molecules can be accomplished by contacting the hapten-labeled NPP with a primary anti-hapten antibody. In one example, the primary anti-hapten antibody (such as a mouse anti-hapten antibody) is directly labeled with an enzyme. In another example, a secondary anti-antibody (such as a goat anti-mouse IgG antibody) conjugated to an enzyme is used for signal amplification. In other examples, the hapten is biotin and is detected by contacting the hapten-labeled NPP with avidin or streptavidin conjugated to an enzyme, such as horseradish peroxidase (HRP) or alkaline phosphatase (AP).

Additional examples of detectable labels include fluorescent molecules (or fluorochromes). Numerous fluorochromes are known to those of ordinary skill in the art, and can be selected, for example from Life Technologies (formerly Invitrogen), e.g., see, The Handbook—A Guide to Fluorescent Probes and Labeling Technologies). Examples of particular fluorophores that can be attached (for example, chemically conjugated) to a nucleic acid molecule (such as an NPP) are provided in U.S. Pat. No. 5,866,366 to Nazarenko et al., such as 4-acetamido-4'-isothiocyanatostilbene-2,2' disulfonic acid, acridine and derivatives such as acridine and acridine isothiocyanate, 5-(2'-aminoethyl)aminonaphthalene-1-sulfonic acid (EDANS),4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumarin 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); 2',7'-difluorofluorescein (OREGON GREEN®); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, rhodamine green, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other suitable fluorophores include thiol-reactive europium chelates which emit at approximately 617 nm (Heyduk and Heyduk, *Analyt. Biochem.* 248:216-27, 1997; *J. Biol. Chem.* 274:3315-22, 1999), as well as GFP, LISSAMINE, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. Other fluorophores known to those of ordinary skill in the art can also be used, for example those available from Life Technologies (Invitrogen; Molecular Probes (Eugene, Oreg.)) and including the ALEXA FLUOR® series of dyes (for example, as described in U.S. Pat. Nos. 5,696,157, 6,130,101 and 6,716,979), the BODIPY series of dyes (dipyrrometheneboron difluoride dyes, for example as described in U.S. Pat. Nos. 4,774,339, 5,187,288, 5,248,782, 5,274,113, 5,338,854, 5,451,663 and 5,433,896), Cascade Blue (an amine reactive derivative of the sulfonated pyrene described in U.S. Pat. No. 5,132,432) and Marina Blue (U.S. Pat. No. 5,830,912).

In addition to the fluorochromes described above, a fluorescent label can be a fluorescent nanoparticle, such as a semiconductor nanocrystal, e.g., a QUANTUM DOT (obtained, for example, from Life Technologies (QuantumDot Corp, Invitrogen Nanocrystal Technologies, Eugene, Oreg.)); see also, U.S. Pat. Nos. 6,815,064; 6,682,596; and 6,649,138). Semiconductor nanocrystals are microscopic particles having size-dependent optical and/or electrical properties. When semiconductor nanocrystals are illuminated with a primary energy source, a secondary emission of energy occurs of a frequency that corresponds to the bandgap of the semiconductor material used in the semiconductor nanocrystal. This emission can be detected as colored light of a specific wavelength or fluorescence. Semiconductor nanocrystals with different spectral characteristics are described in e.g., U.S. Pat. No. 6,602,671. Semiconductor nanocrystals can be coupled to a variety of biological molecules (including dNTPs and/or nucleic acids) or substrates by techniques described in, for example, Bruchez et al., *Science* 281:2013-2016, 1998; Chan et al., *Science* 281:2016-2018, 1998; and U.S. Pat. No. 6,274,323.

Formation of semiconductor nanocrystals of various compositions are disclosed in, e.g., U.S. Pat. Nos. 6,927,069; 6,914,256; 6,855,202; 6,709,929; 6,689,338; 6,500,622; 6,306,736; 6,225,198; 6,207,392; 6,114,038; 6,048,616; 5,990,479; 5,690,807; 5,571,018; 5,505,928; 5,262,357 and in U.S. Patent Publication No. 2003/0165951 as well as PCT Publication No. 99/26299. Separate populations of semiconductor nanocrystals can be produced that are identifiable based on their different spectral characteristics. For example, semiconductor nanocrystals can be produced that emit light of different colors based on their composition, size or size and composition. For example, quantum dots that emit light at different wavelengths based on size (565 nm, 655 nm, 705 nm, or 800 nm emission wavelengths), which are suitable as fluorescent labels in the probes disclosed herein are available from Life Technologies (Carlsbad, Calif.).

Additional labels include, for example, radioisotopes (such as $^3$H), metal chelates such as DOTA and DPTA chelates of radioactive or paramagnetic metal ions like $Gd^{3+}$, and liposomes.

Detectable labels that can be used with nucleic acid molecules (such as an NPP) also include enzymes, for example HRP, AP, acid phosphatase, glucose oxidase, β-galactosidase, β-glucuronidase, or β-lactamase. Where the detectable label includes an enzyme, a chromogen, fluorogenic compound, or luminogenic compound can be used in combination with the enzyme to generate a detectable signal (numerous of such compounds are commercially available, for example, from Life Technologies, Carlsbad, Calif.). Particular examples of chromogenic compounds include diaminobenzidine (DAB), 4-nitrophenylphosphate (pNPP), fast red, fast blue, bromochloroindolyl phosphate (BCIP), nitro blue tetrazolium (NBT), BCIP/NBT, AP Orange, AP blue, tetramethylbenzidine (TMB), 2,2'-azino-di-[3-ethyl-benzothiazoline sulphonate] (ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue and tetrazolium violet.

Alternatively, an enzyme can be used in a metallographic detection scheme. Metallographic detection methods include using an enzyme, such as alkaline phosphatase, in combination with a water-soluble metal ion and a redox-inactive substrate of the enzyme. The substrate is converted to a redox-active agent by the enzyme, and the redox-active agent reduces the metal ion, causing it to form a detectable precipitate. (See, for example, U.S. Patent Application Publication No. 2005/0100976, PCT Publication No. 2005/003777 and U.S. Patent Application Publication No. 2004/0265922). Metallographic detection methods also include using an oxido-reductase enzyme (such as horseradish peroxidase) along with a water soluble metal ion, an oxidizing agent and a reducing agent, again to form a detectable precipitate. (See, for example, U.S. Pat. No. 6,670,113).

In some embodiments, the detectable label is attached to or incorporated in the NPP at the 5' end or the 3' end of the probe (e.g., the NPP is an end-labeled probe). In other examples the detectable label is incorporated in the NPP at an internal position, such as 1, 2, 3, 4, 5, 6, 7, 8, 9, 10, 11, 12, 13, 14, 15, or more bases from the 5' end of the NPP or 1, 2, 3, 4, 5, 6, 7, 8, 9, 10, 11, 12, 13, 14, 15, or more bases from the 3' end of the NPP.

V. Samples

The samples of use in the disclosed methods include any specimen that includes nucleic acid (such as genomic DNA, cDNA, viral DNA or RNA, rRNA, tRNA, snRNA, snoRNA, mRNA, miRNA, siRNA, piRNA, oligonucleotides, nucleic acid fragments, modified nucleic acids, synthetic nucleic acids, or the like). In some examples, the disclosed methods include obtaining the sample prior to analysis of the sample. In some examples, the disclosed methods include selecting a subject having a tumor, and then in some examples further selecting one or more target small non-coding RNAs and mRNAs to detect based on the subject's tumor, for example, to determine a diagnosis or prognosis for the subject or for selection of one or more therapies.

Exemplary samples include, without limitation, cells, cell lysates, blood smears, cytocentrifuge preparations, cytology smears, bodily fluids (e.g., blood, saliva, sputum, urine, etc.), tissue biopsies (e.g., tumor biopsies), fine-needle aspirates, and/or tissue sections (e.g., cryostat tissue sections and/or paraffin-embedded tissue sections). Methods of obtaining a sample from a subject are known in the art. For example, methods of obtaining tissue or cell samples are routine. Exemplary samples may be obtained from normal cells or tissues, or from neoplastic cells or tissues. Neoplasia is a biological condition in which one or more cells have undergone characteristic anaplasia with loss of differentiation, increased rate of growth, invasion of surrounding tissue, and which cells may be capable of metastasis. In particular examples, a biological sample includes a tumor sample, such as a sample containing neoplastic cells.

Exemplary neoplastic cells or tissues may be included in or isolated from solid tumors, including lung cancer (e.g., non-small cell lung cancer, such as lung squamous cell carcinoma), breast carcinomas (e.g. lobular and duct carcinomas), adrenocortical cancer, ameloblastoma, ampullary cancer, bladder cancer, bone cancer, cervical cancer, cholangioma, colorectal cancer, endometrial cancer, esophageal cancer, gastric cancer, glioma, granular call tumor, head and neck cancer, hepatocellular cancer, hydatiform mole, lymphoma, melanoma, mesothelioma, myeloma, neuroblastoma, oral cancer, osteochondroma, osteosarcoma, ovarian cancer, pancreatic cancer, pilomatricoma, prostate cancer, renal cell cancer, salivary gland tumor, soft tissue tumors, Spitz nevus, squamous cell cancer, teratoid cancer, and thyroid cancer. Exemplary neoplastic cells may also be included in or isolated from hematological cancers including leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, and myelodysplasia.

For example, a sample from a tumor that contains cellular material can be obtained by surgical excision of all or part of the tumor, by collecting a fine needle aspirate from the tumor, as well as other methods known in the art. In some examples, a tissue or cell sample is applied to a substrate and analyzed to determine presence of one or more target miRNAs and mRNAs. A solid support useful in a disclosed method need only bear the biological sample and, optionally, but advantageously, permit the convenient detection of components (e.g., proteins and/or nucleic acid sequences) in the sample. Exemplary supports include microscope slides (e.g., glass microscope slides or plastic microscope slides), coverslips (e.g., glass coverslips or plastic coverslips), tissue culture dishes, multi-well plates, membranes (e.g., nitrocellulose or polyvinylidene fluoride (PVDF)) or BIACORE™ chips.

The disclosed methods are sensitive and specific and allow detection of target mRNA and/or small non-coding RNA in a sample containing even a limited number of cells. For example, expression of a target mRNA or target miRNA can be detected in as few as 1000 cells (such as a sample including 1000 or more cells, such as 1000, 2000, 3000, 4000, 5000, 6000, 7000, 8000, 9000, 10,000, 15,000, 20,000, 50,000, or more cells). In some examples, expression of a target mRNA or target miRNA can be detected in about 1000 to 100,000 cells, for example about 1000 to 50,000, 1000 to 15,000, 1000 to 10,000, 1000 to 5000, 3000 to 50,000, 6000 to 30,000, or 10,000 to 50,000 cells). In other examples, expression of a target mRNA or target miRNA can be detected in about 1 to 1000 cells (such as about 1 to 500 cells, about 1 to 250 cells, about 1 to 100 cells, about 1 to 50 cells, about 1 to 25 cells, or about 1 cell).

The samples described herein can be prepared using any method now known or hereafter developed in the art. In some examples, cells in the sample are lysed or permeabilized in an aqueous solution (for example using a lysis buffer). The aqueous solution or lysis buffer includes detergent (such as sodium dodecyl sulfate) and one or more chaotropic agents (such as formamide, guanidinium HCl, guanidinium isothiocyanate, or urea). The solution may also contain a buffer (for example SSC). In some examples, the lysis buffer includes about 15% to 25% formamide (v/v), about 0.01% to 0.1% SDS, and about 0.5-6×SSC (for example, about 3×SSC). The buffer may optionally include tRNA (for example, about 0.001 to about 2.0 mg/ml) or a ribonuclease. The lysis buffer may also include a pH indicator, such as Phenol Red. In a particular example, the lysis buffer includes 20% formamide, 3×SSC (79.5%), 0.05% SDS, 1 μg/ml tRNA, and 1 mg/ml Phenol Red. Cells are incubated in the aqueous solution for a sufficient period of time (such as about 1 minute to about 60 minutes, for example about 5 minutes to about 20 minutes, or about 10 minutes) and at a sufficient temperature (such as about 22° C. to about 115° C., for example, about 37° C. to about 105° C., or about 90° C. to about 100° C.) to lyse or permeabilize the cell. In some examples, lysis is performed at about 95° C. In some examples, the lysis step includes incubating the sample at about 95° C. for about 5-15 minutes to denature RNA in the sample, but not genomic DNA. In other examples, the lysis step includes incubating the sample at about 105° C. for about 5-15 minutes to denature both RNA and genomic DNA in the sample.

In some examples, the crude cell lysis is used directly without further purification. The cells may be lysed in the presence or absence of one or more of the disclosed probes. If the cells are lysed in the absence of probe, the one or more probes can be subsequently added to the crude lysate. In other examples, nucleic acids (such as miRNA and/or mRNA) are isolated from the cell lysate prior to contacting the lysate prior to contacting with one or more of the disclosed probes.

In other examples, tissue samples are prepared by fixing and embedding the tissue in a medium or include a cell suspension is prepared as a monolayer on a solid support (such as a glass slide), for example by smearing or centrifuging cells onto the solid support. In further examples, fresh frozen (for example, unfixed) tissue or tissue sections may be used in the methods disclosed herein. In particular examples, FFPE tissue sections are used in the disclosed methods.

In some examples an embedding medium is used. An embedding medium is an inert material in which tissues and/or cells are embedded to help preserve them for future analysis. Embedding also enables tissue samples to be sliced into thin sections. Embedding media include paraffin, celloidin, OCT compound, agar, plastics, or acrylics. Many embedding media are hydrophobic; therefore, the inert material may need to be removed prior to analysis, which utilizes primarily hydrophilic reagents. The term deparaffinization or dewaxing is broadly used herein to refer to the partial or complete removal of any type of embedding medium from a biological sample. For example, paraffin-embedded tissue sections are dewaxed by passage through organic solvents, such as toluene, xylene, limonene, or other suitable solvents. In other examples, paraffin-embedded tissue sections are utilized directly (e.g., without a dewaxing step).

Tissues can be fixed by any suitable process, including perfusion or by submersion in a fixative. Fixatives can be classified as cross-linking agents (such as aldehydes, e.g., formaldehyde, paraformaldehyde, and glutaraldehyde, as well as non-aldehyde cross-linking agents), oxidizing agents (e.g., metallic ions and complexes, such as osmium tetroxide and chromic acid), protein-denaturing agents (e.g., acetic acid, methanol, and ethanol), fixatives of unknown mechanism (e.g., mercuric chloride, acetone, and picric acid), combination reagents (e.g., Carnoy's fixative, methacarn, Bouin's fluid, B5 fixative, Rossman's fluid, and Gendre's fluid), microwaves, and miscellaneous fixatives (e.g., excluded volume fixation and vapor fixation). Additives may also be included in the fixative, such as buffers, detergents, tannic acid, phenol, metal salts (such as zinc chloride, zinc sulfate, and lithium salts), and lanthanum.

The most commonly used fixative in preparing tissue or cell samples is formaldehyde, generally in the form of a formalin solution (4% formaldehyde in a buffer solution, referred to as 10% buffered formalin). In one example, the fixative is 10% neutral buffered formalin.

VI. Target Nucleic Acids

Target nucleic acids include mRNA and small non-coding RNA. Non-coding RNA are RNA that are not translated into protein and include well known RNA types such as ribosomal RNA (rRNA), transfer RNA (tRNA), small nuclear RNA (snRNA), and small nucleolar RNA (snoRNA). However, additional types of non-coding RNA, including small non-coding RNAs have recently been identified (e.g., Sana et al., *J. Transl. Med.* 10:103, 2012). In some embodiments, small non-coding RNA regulate (for example, increase or decrease) translation of RNA. Small non-coding RNA encompasses any non-coding RNA of about 60 nucleotides or less, such as under 60, under 55, under 50, under 45, under 40, under 35, under 30, under 25, under 20, under 15, or under 10 nucleotides in length. In some examples, small non-coding RNA are between about 10-60, about 15-50, about 15-40, about 15-30, about 20-50, about 20-40, about 20-35, about 20-30, about 20-25, or about 25-30 nucleotides in length (such as 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides). Small non-coding RNAs include but are not limited to miRNA, siRNA, piRNA, tiRNA, crasiRNA, and tel-sRNA. In some embodiments, small non-coding RNA includes miRNA and siRNA or miRNA alone. In some embodiments, small non-coding RNA excludes rRNA and tRNA.

In specific non-limiting examples, a target nucleic acid (such as a target mRNA or target small non-coding RNA) associated with a neoplasm (for example, a cancer) or other disease or disorder is selected. Numerous chromosome abnormalities (including translocations and other rearrangements, reduplication or deletion) or mutations have been identified in neoplastic cells, especially in cancer cells, such as B cell and T cell leukemias, lymphomas, breast cancer, colon cancer, neurological cancers and the like.

In some examples, a target mRNA includes GAPDH (e.g., GenBank Accession No. NM_002046), PPIA (e.g., GenBank Accession No. NM_021130), RPLP0 (e.g., GenBank Accession Nos. NM_001002 or NM_053275), RPL19 (e.g., GenBank Accession No. NM_000981), ZEB1 (e.g., GenBank Accession No. NM_030751), Zeb2 (e.g., GenBank Accession Nos. NM_001171653 or NM_014795), CDH1 (e.g., GenBank Accession No. NM_004360), CDH2 (e.g., GenBank Accession No. NM_007664), VIM (e.g., GenBank Accession No. NM_003380), ACTA2 (e.g., GenBank Accession No. NM_001141945 or NM_001613), CTNNB1 (e.g., GenBank Accession No. NM_001904, NM_001098209, or NM_001098210), KRT8 (e.g., GenBank Accession No. NM_002273), SNAI1 (e.g., GenBank Accession No. NM_005985), SNAI2 (e.g., GenBank Accession No. NM_003068), TWIST1 (e.g., GenBank Accession No. NM_000474), CD44 (e.g., GenBank Accession No. NM_000610, NM_001001389, NM_00100390, NM_001202555, NM_001001391, NM_001202556, NM_001001392, NM_001202557), CD24 (e.g., GenBank Accession No. NM_013230), FN1 (e.g., GenBank Accession No. NM_212474, NM_212476, NM_212478, NM_002026, NM_212482, NM_054034), IL6 (e.g., GenBank Accession No. NM_000600), MYC (e.g., GenBank Accession No. NM_002467), VEGFA (e.g., GenBank Accession No. NM_001025366, NM_001171623, NM_003376, NM_001171624, NM_001204384, NM_001204385, NM_001025367, NM_001171625, NM_001025368, NM_001171626, NM_001033756, NM_001171627, NM_001025370, NM_001171628, NM_001171622, NM_001171630), HIF1A (e.g., GenBank Accession No. NM_001530, NM_181054), EPAS1 (e.g., GenBank Accession No. NM_001430), ESR2 (e.g., GenBank Accession No. NM_001040276, NM_001040275, NM_001214902, NM_001437, NM_001214903), PRKCE (e.g., GenBank Accession No. NM_005400), EZH2 (e.g., GenBank Accession No. NM_001203248, NM_152998, NM_001203247, NM_004456, NM_001203249), DAB21P (e.g., GenBank Accession No. NM_032552, NM_138709), B2M (e.g., GenBank Accession No. NM_004048), and SDHA (e.g., GenBank Accession No. NM_004168).

In other examples, a target miRNA includes hsa-miR-205 (MIR205, e.g., GenBank Accession No. NR_029622), hsa-miR-324 (MIR324, e.g., GenBank Accession No. NR_029896), hsa-miR-301a (MIR301A, e.g., GenBank Accession No. NR_029842), hsa-miR-106b (MIR106B, e.g., GenBank Accession No. NR_029831), hsa-miR-877 (MIR877, e.g., GenBank Accession No. NR_030615), hsa-miR-339 (MIR339, e.g., GenBank Accession No. NR_029898), hsa-miR-10b ($MIR_{10}B$, e.g., GenBank Accession No. NR_029609), hsa-miR-185 (MIR185, e.g., GenBank Accession No. NR_029706), hsa-miR-27b ($MIR_{27}B$, e.g., GenBank Accession No. NR_029665), hsa-miR-492 (MIR492, e.g., GenBank Accession No. NR_030171), hsa-miR-146a (MIR146A, e.g., GenBank Accession No. NR_029701), hsa-miR-200a (MIR200A, e.g., GenBank Accession No. NR_029834), hsa-miR-30c (e.g., GenBank Accession No. NR_029833, NR_029598), hsa-miR-29c ($MIR_{29}C$, e.g., GenBank Accession No. NR_029832), hsa-miR-191 (MIR191, e.g., GenBank Accession No. NR_029690), or hsa-miR-655 (MIR655, e.g., GenBank Accession No. NR_030391).

One of ordinary skill in the art can identify additional target mRNAs and/or additional target small non-coding RNAs (such as miRNAs) which can be detected utilizing the methods disclosed herein.

VII. Assay Output

In some embodiments, the disclosed methods include determining presence or an amount of one or more mRNA and one or more small non-coding RNA in a sample. The results of the test are provided to a user (such as a scientist, clinician or other health care worker, laboratory personnel, or patient) in a perceivable output that provides information about the results of the test. In some examples, the output can be a paper output (for example, a written or printed output), a display on a screen, a graphical output (for example, a graph, chart, or other diagram), or an audible output. In one example, the output is a table or graph including a qualitative or quantitative indicator of presence or amount (such as a normalized amount) of an mRNA or miRNA detected (or not detected) in the sample. In other examples the output is a map or image of signal present on a substrate (for example, a digital image of fluorescence from an array).

In some examples, the output is a numerical value, such as an amount of an mRNA or miRNA in a sample. In additional examples, the output is a graphical representation, for example, a graph that indicates the value (such as amount or relative amount) of an mRNA or miRNA in the sample on a standard curve. In some examples, the output is communicated to the user, for example by providing an output via physical, audible, or electronic means (for example by mail, telephone, facsimile transmission, email, or communication to an electronic medical record).

The output can provide quantitative information (for example, an amount of a particular mRNA or small non-coding RNA or an amount of a particular mRNA or small non-coding RNA relative to a control sample or value) or can provide qualitative information (for example, a determination of presence or absence of a particular mRNA or small non-coding RNA). In additional examples, the output can provide qualitative information regarding the relative amount of an mRNA or small non-coding RNA in the sample, such as identifying an increase or decrease relative to a control or no change relative to a control.

The disclosure is further illustrated by the following non-limiting Examples.

EXAMPLES

Example 1

Analysis of mRNA and miRNA Expression in Cells by Quantitative Nuclease Protection Assay This example demonstrates use of the quantitative nuclease protection assay to simultaneously measure mRNA and miRNA expression in cells.

PC3 cells were aliquoted in 96 well plates at 0-6000 cells per well. Lysis buffer (20% formamide, 3×SSC (79.5%), 0.05% SDS, 1 µg/ml tRNA, and 1 mg/ml Phenol Red), mineral oil (to prevent evaporation) and a cocktail of biotinylated mRNA and miRNA NPPs (final concentration 31.5 pM) were added to the wells. The NPP sequences are shown in Table 2. The sample was heated at 95° C. for 10-15 minutes and then incubated at 37° C. for about 18 hours for RNA-NPP hybridization. S1 nuclease was diluted 1:40 in S1 nuclease buffer (0.25 M sodium acetate, pH 4.5, 1.4 M NaCl, 0.225 M $ZnSO_4$, 0.05% KATHON) and 20 µl was added to the each well. The sample was incubated at 37° C. for 120 minutes to digest unbound nucleic acids. The contents of each well were then transferred to a stop plate containing 10 µS1 stop solution (1.6 N NaOH, 0.135 M EDTA, pH 8.0) in each well and incubated at 95° C. for 15-20 minutes. After cooling at room temperature for 5-10 minutes, 10 µl of neutralization solution (1 M HEPES, pH 7.5, 6×SSC, 1.6 N HCl) was added to each well.

TABLE 2 mRNA and miRNA NPP sequences

| Target | NPP Sequence (5'->3') | SEQ ID NO: |
|---|---|---|
| GAPDH | CCGTTGACTCCGACCTTCACCTTCC | 17 |
| PPIA | ACACAAGACTGAGATGCACAAGTGG | 18 |
| RPLP0 | GACAGACACTGGCAACATTGCGGAC | 19 |
| RPL19 | AAGCCTGAGCATACTCATGGCTGCG | 20 |
| ZEB1 | AAAGGCATCTAAACCCAGGCTTCCC | 21 |
| ZEB2 | CTTGTGTGTCACCATATGCCGCTCG | 22 |
| CDH1 | CCAAAGTCCTCGGACACTTCCACTC | 23 |
| CDH2 | TCCGCCACTGATTCTGTACACTGCG | 24 |
| ACTA2 | ACACATAGCTGGAGCTGCTTCACAG | 25 |
| CTNNB1 | TGTGAAGGGCTCCGGTACAACCTTC | 26 |
| KRT8 | CAGCTTCCCATCACGTGTCTCGATC | 27 |
| SNAI1 | GACATTCGGGAGAAGGTCCGAGCAC | 28 |
| SNAI2 | TTGGGTAGCTGGGCGTGGAATGGAG | 29 |
| TWIST1 | CCCGTCTGGGAATCACTGTCCACGG | 30 |
| FN1 | GCTGAACATTGGGTGGTGTCCACTG | 31 |
| EPAS1 | CCCTTGGTGCACAAGTTCTGGTGAC | 32 |
| ESR2 | ACAAAGCCGGGAATCTTCTTGGCCC | 33 |
| PRKCE | CCTCAGATGGTGAGCTTCCAGAAGC | 34 |
| EZH2 | TCAGATTTCTTCCCAGTCTGGCCCA | 35 |
| DAB2IP | CCTCGAAGCAGTAGTCCTGGCCAAG | 36 |
| B2M | CTAAGGCCACGGAGCGAGACATCTC | 37 |
| SDHA | CCAGTGCTCCTCAAAGGGCTTCTTC | 38 |
| hsa-miR-205 | CAGACTCCGGTGGAATGAAGGA | 39 |
| hsa-miR-324-5p | ACACCAATGCCCTAGGGGATGCG | 40 |
| hsa-miR-301a | GCTTTGACAATACTATTGCACTG | 41 |
| hsa-miR-106b | ATCTGCACTGTCAGCACTTTA | 42 |
| hsa-miR-877 | CCCTGCGCCATCTCCTCTAC | 43 |
| hsa-miR-339-3p | CGGCTCTGTCGTCGAGGCGCTCA | 44 |
| hsa-miR-10b | CACAAATTCGGTTCTACAGGGTA | 45 |
| hsa-miR-185 | TCAGGAACTGCCTTTCTCTCCA | 46 |
| hsa-miR-27b | GTTCACCAATCAGCTAAGCTCT | 47 |
| hsa-miR-492 | AAGAATCTTGTCCCGCAGGTCCT | 48 |
| hsa-miR-146a | AACCCATGGAATTCAGTTCTCA | 49 |
| hsa-miR-200a | TCCAGCACTGTCCGGTAAGATG | 50 |
| ANT | GTTGTGATGGGTCCCAAAGAAATCC | 51 |
| hsa-miR-339-5p | CGTGAGCTCCTGGAGGACAGGGA | 52 |
| hsa-miR-30c | GCTGAGAGTGTAGGATGTTTACA | 53 |
| hsa-miR-29c | GAACACCAGGAGAAATCGGTCA | 54 |
| hsa-miR-191 | CAGCTGCTTTTGGGATTCCGTTG | 55 |
| hsa-miR-655 | AAAGAGGTTAACCATGTATTAT | 56 |

A 96 well ArrayPlate having anchors at pre-determined locations was prepared by washing 6 times with 20× wash solution (20×SSC, 0.95% TWEEN-20, 0.05% KATHON) diluted by 1:20. Then, 40 µl of ArrayPlate programming solution containing the programming linkers (5 nM) was added to each well and incubated at 60° C. for 60 minutes. The programming linkers included 20-25 nucleotides complementary to a portion of the NPP sequence shown above, and 25 nucleotides complementary to a portion of the anchor molecule on the array. The neutralized samples were transferred to the ArrayPlate and incubated at 50° C. for 16-24 hours to allow probe hybridization to the ArrayPlate.

Detection enzyme stock (avidin-HRP; HTG Molecular Diagnostics, Part No. 70032) was diluted 1:600 in detection enzyme buffer (1×SSC, 0.5% Tween®-20, 1% non-fat dry milk). The diluted detection enzyme stock was added to the ArrayPlate and incubated at 37° C. for 60 minutes. Luminescent solution was added and the plate was imaged using an OMIX HD (HTG Molecular Diagnostics).

Figure 2:
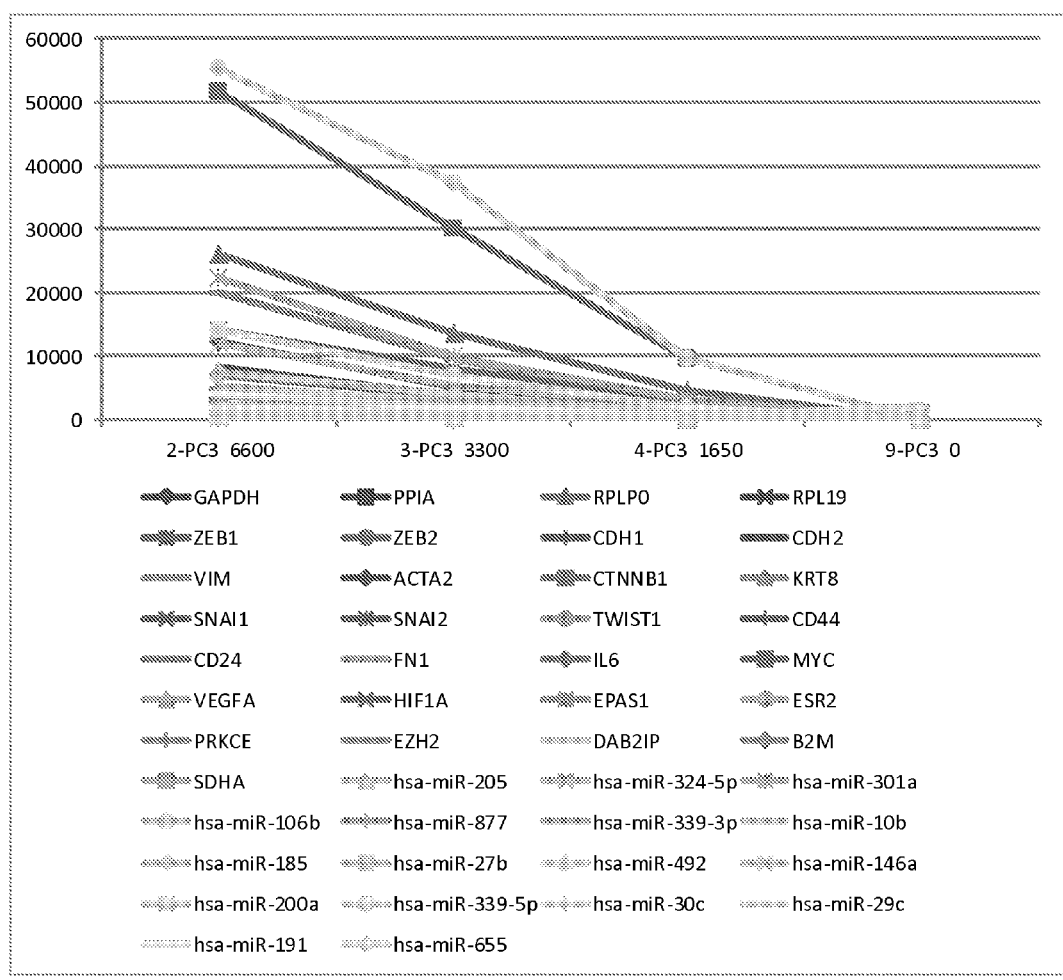
FIG. 2 is a graph of mRNA and miRNA detected in samples with increasing numbers of PC3 cells (0, 1650, 3300, or 6600 cells) per sample.

Using this assay, both mRNA and miRNA were detected in the cells. A titration experiment demonstrated that the assay was linear and sensitive, capable of measuring target molecules in as few as 1650 cells per sample (FIG. 2).

Example 2

Comparison of Simultaneous Detection of mRNA and miRNA in Stained and Unstained Tissue Sections This example describes a comparison of co-detection of mRNA and miRNA in unstained and H&E stained tissue sections.

The samples included paired 3 µm FFPE sections of breast tumor biopsy from a single individual, where one section was unstained and one sample was stained with H&E. FFPE samples were prepared by scraping the section into a microcentrifuge tube, adding 100 µl of lysis buffer (20% formamide, 3×SSC (79.5%), 0.05% SDS, 1 µg/ml tRNA, and 1 mg/ml Phenol Red) and mineral oil, and incubated at 95° C. for 15 minutes. After allowing to cool to room temperature, 5 of lysis buffer including a cocktail of mRNA and miRNA NPPs (final concentration 31.5 pM) was added. The remainder of the assay was performed as described in Example 1.

Figure 3A:
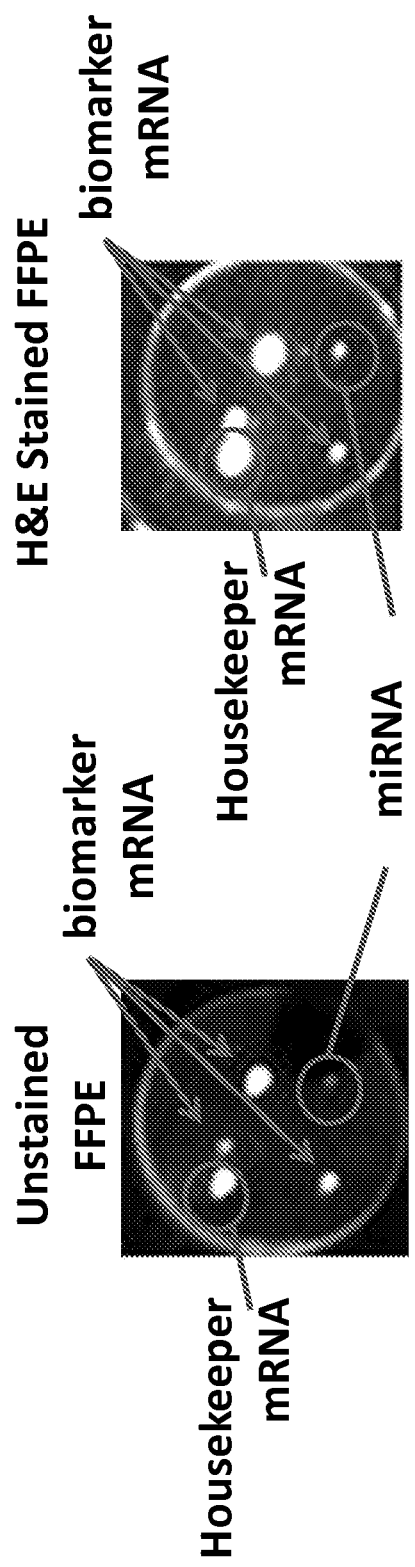
FIG. 3A is a pair of digital images of a qNPA assay array utilizing either an unstained section of a breast tumor biopsy (left) or a hematoxylin and eosin (H&E) stained section from the same breast tumor biopsy (right).
Figure 3B:
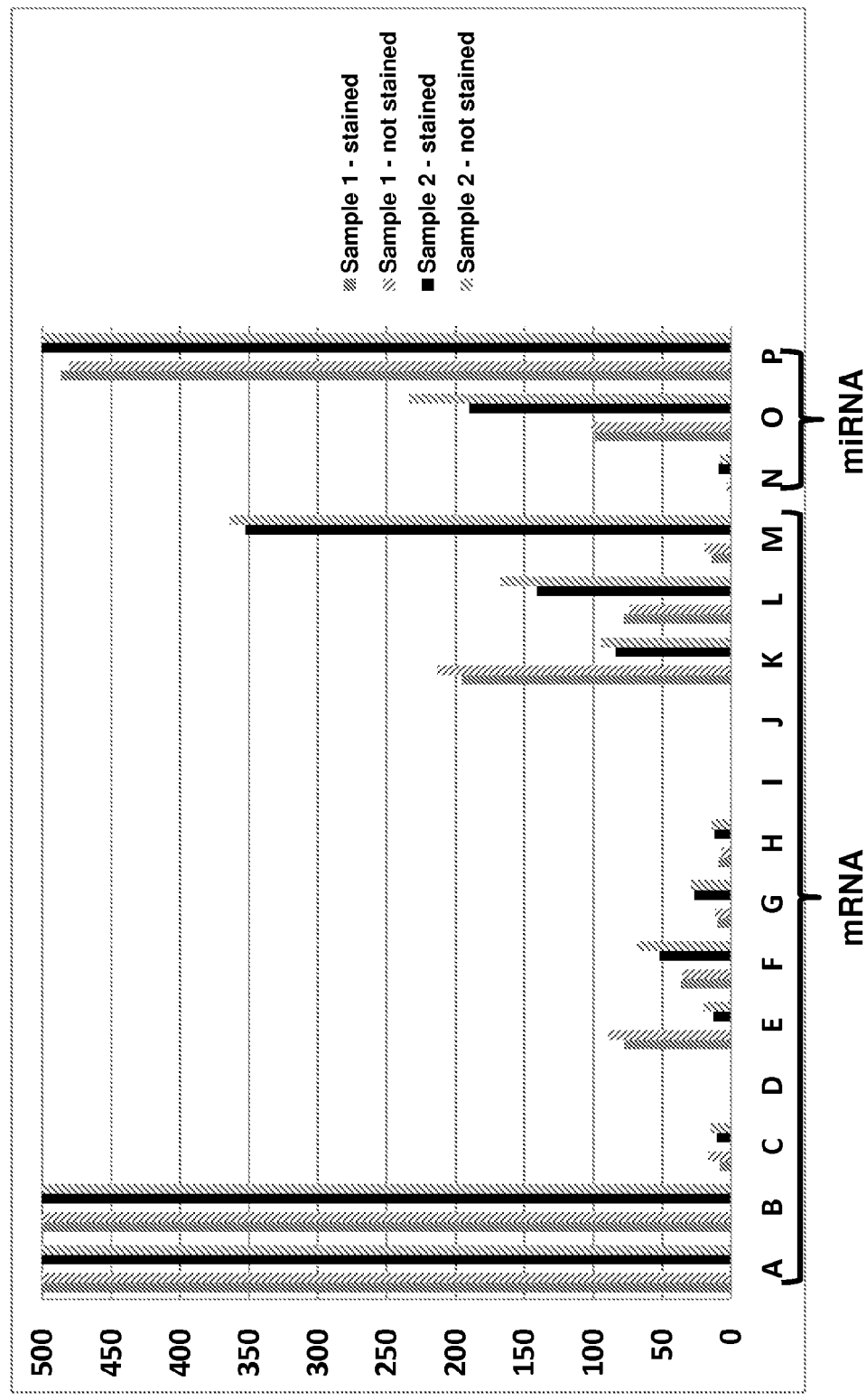
FIG. 3B is a bar graph showing expression of 13 mRNAs and 3 miRNAs in paired unstained and H&E stained sections from two different individuals following normalization of each mRNA or miRNA to expression of an mRNA housekeeping gene in the sample.

As shown in FIG. 3A, the unstained section apparently had lower expression of mRNAs and miRNAs. Following imaging of the array, the expression of selected mRNAs and miRNAs was normalized to expression of a housekeeping RNA (GAPDH). Normalization to the housekeeping RNA demonstrated that expression of the mRNAs and miRNAs was substantially the same between the stained and unstained samples from two different individuals (FIG. 3B). The apparent differences in expression shown in FIG. 3A may be the result of differing cellularity between the two starting tissue samples or the result of variability in sample preparation.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. A method of co-detecting messenger RNA (mRNA) and small non-coding RNA in a sample, comprising:
   contacting a sample at about 37-42° C. with at least 10 nuclease protection probes (NPPs), wherein the at least 10 NPPs comprise (i) at least one NPP that specifically binds to at least one target mRNA and comprises a target mRNA-specific portion consisting of 15-30 nucleotides and (ii) at least one NPP that specifically binds to at least one target small non-coding RNA and comprises a target small non-coding RNA-specific portion consisting of 18-23 nucleotides, under conditions sufficient for the NPPs to specifically bind to the target mRNA or target small non-coding RNA, and wherein each of the at least 10 NPPs comprises a detectable label;
   contacting the sample with a nuclease specific for single-stranded nucleic acid molecules at about 37-50° C. under conditions sufficient to remove unbound nucleic acid molecules; and
   detecting a presence of at least one NPP that specifically binds to the at least one target mRNA and at least one NPP that specifically binds to the at least one small non-coding RNA, thereby co-detecting the at least one mRNA and the at least one small non-coding RNA in the sample, wherein the at least one mRNA and the at least one small non-coding RNA are detectable in as few as 2000 cells.

2. The method of claim 1, wherein the small non-coding RNA comprises microRNA (miRNA).

3. The method of claim 1, wherein the method does not include an amplification step.

4. The method of claim 1, wherein the nuclease specific for single-stranded nucleic acid molecules comprises a S1 nuclease.

5. The method of claim 1, wherein the at least 10 NPPs are contacted with the sample at about 37° C. for 18 hours.

6. The method of claim 1, wherein each of the at least 10 NPPs comprises the same detectable label.

7. The method of claim 1, wherein at least two NPPs of the at least 10 NPPs comprise different detectable labels.

8. The method of claim 1, wherein the detectable label is selected from the group consisting of a hapten, a fluorescent molecule, an enzyme, or a radioisotope.

9. The method of claim 1, wherein at least one NPP of the at least 10 NPPs comprises one or more modified nucleotides.

10. The method of claim 1, wherein detecting the presence of at least one NPP that specifically binds to the at least one target mRNA and at least one NPP that specifically binds to the at least one small non-coding RNA comprises:
    contacting the sample with a surface comprising multiple spatially discrete regions, each region comprising at least one anchor in association with a bifunctional linker comprising a first portion that specifically binds to the anchor and a second portion that specifically binds to one of the at least 10 NPPs, under conditions sufficient for the NPPs to specifically bind to the second portion of the bifunctional linker; and
    detecting the presence of the detectable label.

11. The method of claim 10, wherein the conditions sufficient for the NPPs to specifically bind to the second portion of the bifunctional linker comprise contacting the sample with the surface at 50° C. for 16 hours.

12. The method of claim 10, wherein the anchor comprises a first region that specifically binds to the bifunctional linker and a second region comprising a spacer molecule.

13. The method of claim 1, wherein detecting the presence of at least one NPP that specifically binds to the at least one target mRNA and at least one NPP that specifically binds to the at least one small non-coding RNA comprises:
contacting the sample with a population of surfaces, wherein the population of surfaces further comprises subpopulations of surfaces, and wherein each subpopulation of surfaces comprises at least one anchor in association with a bifunctional linker comprising a first portion that specifically binds to the anchor and a second portion that specifically binds to one of the at least 10 NPPs, under conditions sufficient for the NPPs to specifically bind to the second portion of the bifunctional linker; and
detecting the presence of the detectable label.

14. The method of claim 13, wherein the subpopulations of surfaces comprise:
a first surface comprising substantially similar first anchors stably attached to the first surface and a second surface comprising substantially similar second anchors attached to the second surface, wherein the first anchors and second anchors are substantially different from each other;
a first bifunctional linker that has a first portion complementary to the first anchor and a second portion complementary to at least one of the at least 10 NPPs; and
a second bifunctional linker that has a first portion complementary to the second anchor and a second portion complementary to at least one of the at least 10 NPPs.

15. The method of claim 13, wherein the population of surfaces is a population of beads or microfluidic channels.

16. The method of claim 1, wherein detecting the presence of at least one NPP that specifically binds to the at least one target mRNA and at least one NPP that specifically binds to the at least one small non-coding RNA comprises:
contacting the sample with a surface comprising multiple spatially discrete regions, each region comprising at least one oligonucleotide that specifically binds to at least a portion of one of the at least 10 NPPs, under conditions sufficient for the NPPs to specifically bind to the oligonucleotide; and
detecting the presence of the detectable label.

17. The method of claim 1, wherein detecting the presence of at least one NPP that specifically binds to the at least one target mRNA and at least one NPP that specifically binds to the at least one small non-coding RNA comprises:
contacting the sample with a population of surfaces, wherein the population of surfaces further comprises subpopulations of surfaces, and wherein each subpopulation of surfaces comprises at least one oligonucleotide that specifically binds to at least a portion of one of the at least 10 NPPs, under conditions sufficient for the NPPs to specifically bind to the oligonucleotide; and
detecting the presence of the detectable label.

18. The method of claim 17, wherein the subpopulations of surfaces comprise:
a first surface comprising substantially similar first oligonucleotides stably attached to the first surface, wherein the first oligonucleotide specifically binds to at least a portion of a first NPP;
and a second surface comprising substantially similar second oligonucleotides attached to the second surface, wherein the second oligonucleotide specifically binds to at least a portion of a second NPP,
wherein the first oligonucleotide and second oligonucleotide are substantially different from each other.

19. The method of claim 1, further comprising lysing the sample.

20. The method of claim 1, wherein the sample is selected from the group consisting of a tissue, a fixed tissue, a tumor biopsy, cells, blood, and a bodily fluid.

21. The method of claim 1, wherein the at least 10 NPPs comprise at least two NPPs that specifically bind to at least two target mRNAs and at least two NPPs that specifically bind to at least two target small non-coding RNAs.

22. The method of claim 1, wherein contacting the sample with at least 10 NPPs further comprises contacting the sample with at least 20 NPPs comprising at least two NPPs that specifically bind to at least two target mRNAs and at least two NPPs that specifically bind to at least two target small non-coding RNAs.

* * * * *